(12) United States Patent
Bly et al.

(10) Patent No.: US 10,416,624 B2
(45) Date of Patent: Sep. 17, 2019

(54) METHODS AND SYSTEMS FOR SELECTING SURGICAL APPROACHES

(71) Applicant: UNIVERSITY OF WASHINGTON THROUGH ITS CENTER FOR COMMERCIALIZATION, Seattle, WA (US)

(72) Inventors: Randall Bly, Seattle, WA (US); Blake Hannaford, Seattle, WA (US); Kris S. Moe, Seattle, WA (US)

(73) Assignee: University of Washington Through its Center for Commercialization, Seattle, WA (US)

( * ) Notice: Subject to any disclaimer, the term of this patent is extended or adjusted under 35 U.S.C. 154(b) by 646 days.

(21) Appl. No.: 14/647,639

(22) PCT Filed: Dec. 13, 2013

(86) PCT No.: PCT/US2013/075115
§ 371 (c)(1),
(2) Date: May 27, 2015

(87) PCT Pub. No.: WO2014/093880
PCT Pub. Date: Jun. 19, 2014

(65) Prior Publication Data
US 2015/0297309 A1    Oct. 22, 2015

Related U.S. Application Data

(60) Provisional application No. 61/737,008, filed on Dec. 13, 2012.

(51) Int. Cl.
G05B 15/02    (2006.01)
A61B 34/10    (2016.01)
(Continued)

(52) U.S. Cl.
CPC .............. *G05B 15/02* (2013.01); *A61B 34/10* (2016.02); *B29C 64/386* (2017.08); *G06F 19/00* (2013.01);
(Continued)

(58) Field of Classification Search
CPC .......................... A61B 2034/107; A61B 34/10
See application file for complete search history.

(56) References Cited

U.S. PATENT DOCUMENTS 5,343,391 A * 8/1994 Mushabac .......... A61C 13/0004
433/76
5,562,448 A * 10/1996 Mushabac .......... A61C 13/0004
433/215
(Continued)

OTHER PUBLICATIONS

Alleyne, et al., "Combined transsphenoidal and pterional craniotomy approach to giant pituitary tumors," Surg Neural, vol. 57, No. 6, pp. 380-390, 2002.
(Continued)

*Primary Examiner* — Gregory A Anderson
(74) *Attorney, Agent, or Firm* — McDonnell Boehnen Hulbert & Berghoff LLP

(57) ABSTRACT

Described herein are methods and systems for selecting surgical approaches. One example method involves (1) receiving data indicating (a) one or more surgical target regions and (b) one or more surgical portals; (2) determining a plurality of surgical pathways; (3) determining a plurality of surgical approaches; (4) for each surgical approach in the plurality of surgical approaches, determining at least one approach characteristic, for each determined surgical pathway in the respective surgical approach, determining at least one pathway characteristic, and determining a surgical-approach ranking based on the determined at least one approach characteristic and the determined at least one pathway characteristic; (5) selecting a subset of the plurality
(Continued)

of surgical approaches based on the determined surgical approach rankings; and (6) causing an output device to provide a representation of the selected subset of the plurality of surgical approaches.

18 Claims, 16 Drawing Sheets

(51) Int. Cl.
    *B29C 64/386*     (2017.01)
    *G16H 50/50*     (2018.01)
    *G06F 19/00*     (2018.01)

(52) U.S. Cl.
    CPC ........ *G16H 50/50* (2018.01); *A61B 2034/105* (2016.02); *A61B 2034/107* (2016.02)

(56) References Cited

U.S. PATENT DOCUMENTS

| | | | |
|---|---|---|---|
| 6,064,904 A | | 5/2000 | Yanof |
| 6,261,247 B1 * | | 7/2001 | Ishikawa ............... A61B 5/0031 33/700 |
| 7,967,742 B2 | | 6/2011 | Hoeg |
| 8,160,676 B2 | | 4/2012 | Gielen |
| 8,195,271 B2 * | | 6/2012 | Rahn ........................ A61B 6/12 378/4 |
| 9,603,665 B2 * | | 3/2017 | Bowling ................ A61B 17/16 |
| 9,622,720 B2 * | | 4/2017 | Stolka .................... A61B 90/30 |
| 9,700,292 B2 * | | 7/2017 | Nawana ................. G16H 50/20 |
| 2003/0114862 A1 * | | 6/2003 | Chu ........................ A61B 90/11 606/130 |
| 2006/0004286 A1 * | | 1/2006 | Chang ...................... A61B 5/06 600/435 |
| 2006/0052689 A1 * | | 3/2006 | Scouten ................. G09B 23/30 600/417 |
| 2008/0058838 A1 * | | 3/2008 | Steinberg ......... A61B 17/00234 606/130 |
| 2008/0081982 A1 | | 4/2008 | Simon |
| 2008/0114267 A1 | | 5/2008 | Lloyd |
| 2008/0183074 A1 * | | 7/2008 | Carls .................. A61B 5/04001 600/429 |
| 2009/0221898 A1 * | | 9/2009 | Hillis ................ A61M 37/0069 600/407 |
| 2013/0273501 A1 * | | 10/2013 | Cascone .............. A61C 13/081 433/207 |

OTHER PUBLICATIONS

Balakrishnan, et al., "Applications and outcomes of orbital and transorbital endoscopic surgery," Otolaryngol Head Neck Surg, vol. 144, No. 5, pp. 815-820, 2011.
Bauemschmitt, et al., "Optimal port placement and enhanced guidance in robotically assisted cardiac surgery," Surg Endosc. vol. 21, No. 4, pp. 684-687, 2007.
Beretta, et al., "Image-guided anatomical and morphometric study of supraorbital and transorbital minicraniotomies to the sellar and perisellar regions: comparison with standard techniques," J Neurosurg, vol. 113, No. 5, pp. 975-981, 2010.
Bernardo, "A three-dimensional interactive virtual dissection model to simulate transpetrous surgical avenues," Neurosurgery, vol. 52, No. 3, pp. 499-505, 2003.
Cavalcanti, et al., "Quantitative anatomic study of the transciliary supraorbital approach: benefits of additional orbital osteotomy?" Neurosurgery, vol. 66, No. 6, pp. 205-210, 2010.
Ciporen, et al., "Multiportal endoscopic approaches to the central skull base: a cadaveric study," World Neurosurg, vol. 73, No. 6, pp. 705-712, 2010.
de Notaris, et al., "Preliminary experience with a new three-dimensional computer-based model for the study and the analysis of skull base approaches," Childs Nerv Syst, vol. 26, No. 5, pp. 621-626, 2010.
de Notaris, et al., "The use of a three-dimensional novel computer-based model for analysis of the endonasal endoscopic approach to the midline skull base" World Neurosurg, vol. 75, No. 1, pp. 106-113, 2011.
Filipce, et al., "Quantitative and qualitative analysis of the working area obtained by endoscope and microscope in various approaches to the anterior communicating artery complex using computed tomography-based frameless stereotaxy: a cadaver study," Neurosurgery, . vol. 65, No. 6, pp. 1147-1152, 2009.
Greenfield, et al., "Combined simultaneous endoscopic trans-sphenoidal and endoscopic transventricular resection of a giant pituitary macroadenoma," Minim Invasive Neurosurg, vol. 51, No. 5, pp. 306-309, 2008.
Kakizawa, et al., "Construction of a three-dimensional interactive model of the skull base and cranial nerves," Neurosurgery, vol. 60, No. 5, pp. 901-910; discussion 901-10, 2007.
Kassam, et al., "The front door to meckel's cave: an anteromedial corridor via expanded endoscopic endonasal approach—technical considerations and clinical series," Neurosurgery, vol. 64, No. 3, pp. 71-82, 2009.
Kupferman, et al., "Transantral robotic access to the pituitary gland. Otolaryngol," Head Neck Surg, vol. 141, No. 3, pp. 413-415, 2009.
Lee, et al., "Transoral robotic surgery of the skull base: a cadaver and feasibility study," ORL J Otorhinolaryngol Relat Spec., vol. 72, No. 4, pp. 181-187, 2010.
McCool, et al., "Robotic surgery of the infratemporal fossa utilizing novel suprahyoid port," Laryngoscope, vol. 120, No. 9, pp. 1738-1743, 2010.
Moe, et al., "Transorbital neuroendoscopic surgery," Neurosurgery, vol. 67, No. 3, pp. 16-28, 2010.
Ogata, "A development of surgical simulator for training of operative skills using patient-specific data," Medicine Meets Virtual Reality, vol. 163, pp. 415-421, 2011.
Ojha, "Combined trans-sphenoidal and simultaneous trans-ventricular-endoscopic decompression of a giant pituitary adenoma: case report," Acta Neurochir (Wien), vol. 151, No. 7, pp. 843-847, 2009.
O'Malley, et al., "Robotic anterior and midline skull base surgery: preclinical investigations," Int J Radial Oncol Biol Phys, vol. 69, Suppl 2, pp. S125-S128, 2007.
Prosser, et al., "Quantitative analysis of endoscopic endonasal approaches to the infratemporal fossa," Laryngoscope, vol. 121, No. 8, pp. 1601-1605, 2011.
Qiu, et al., "Virtual reality presurgical planning for cerebral gliomas adjacent to motor pathways in an integrated 3-D stereoscopic visualization of structural MRI and DTI tractography," Acta Neurochir (Wien), vol. 152, No. 11, pp. 1847-1857, 2010.
Romano, et al., "Combined endoscopic transsphenoidal-transventricular approach for resection of a giant pituitary macroadenoma," World Neurosurg, vol. 74, No. 1, pp. 161-164, 2010.
Tolsdorff, et al., "Virtual reality: a new paranasal sinus surgery simulator," Laryngoscope, vol. 120, No. 2, pp. 420-426, 2010.
Woerdeman, et al., "The analysis of intraoperative neurosurgical instrument movement using a navigation log-file," Int J Med Robot, vol. 2, 2, pp. 139-145, 2006.
Zada, et al., "Defining the "edge of the envelope": patient selection in treating complex sellar-based neoplasms via transsphenoidal versus open craniotomy," J Neurosurg vol. 114, No. 2, pp. 286-300, 2011.

* cited by examiner

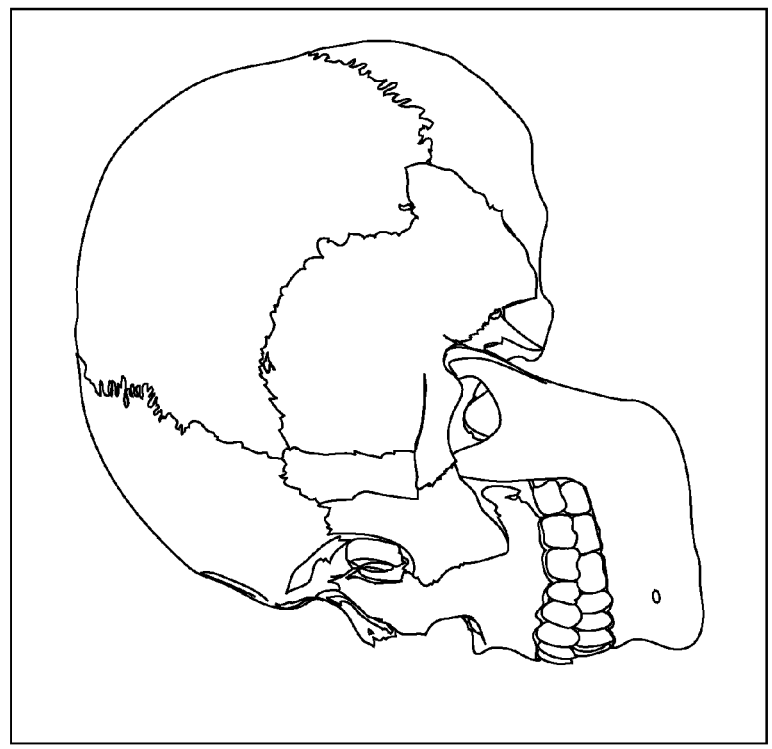
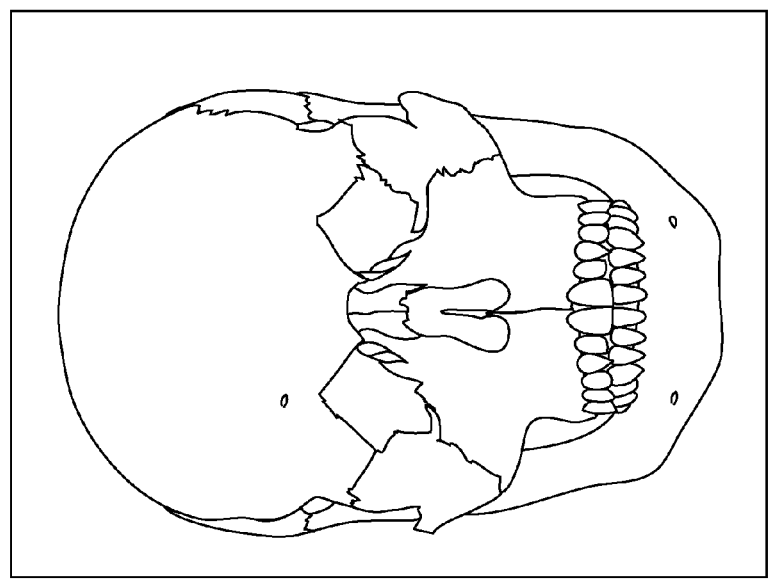
FIG. 4

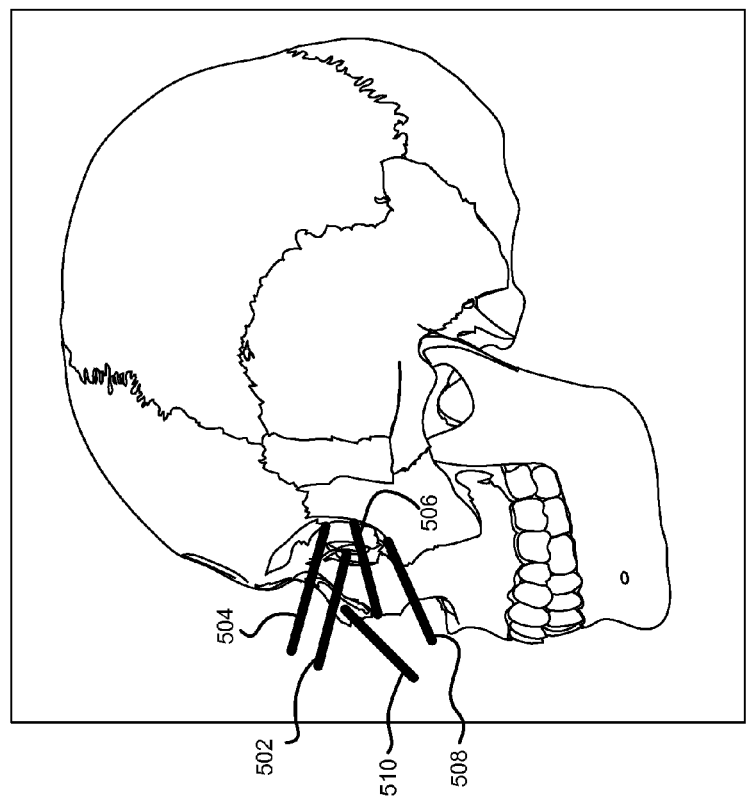
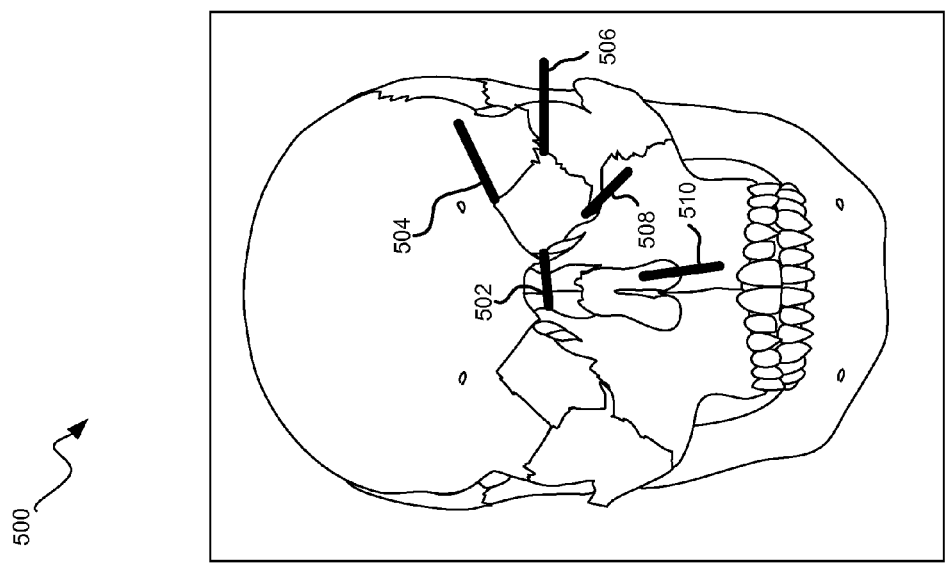
FIG. 5

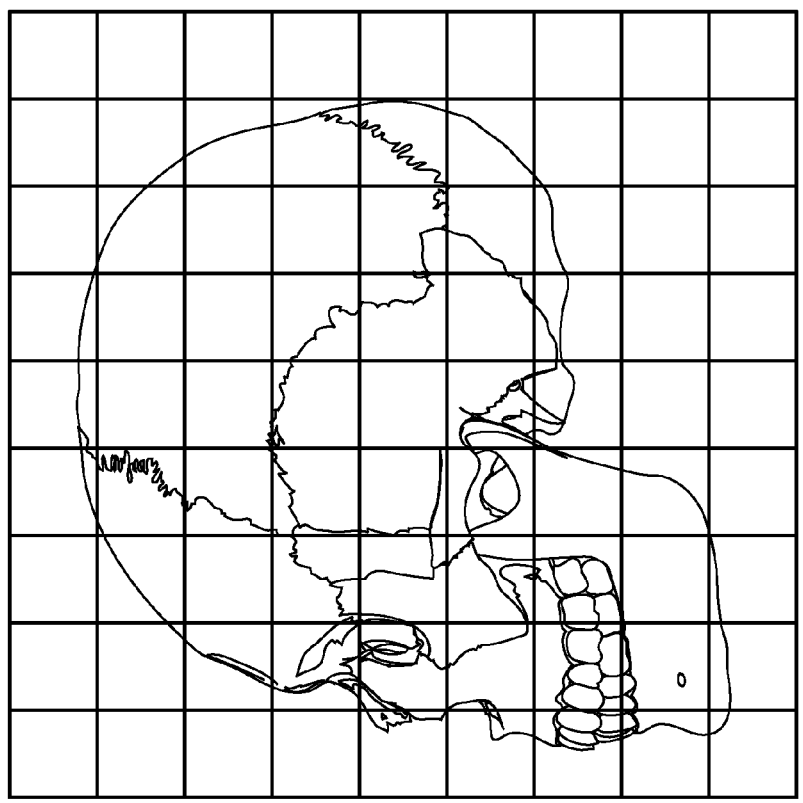
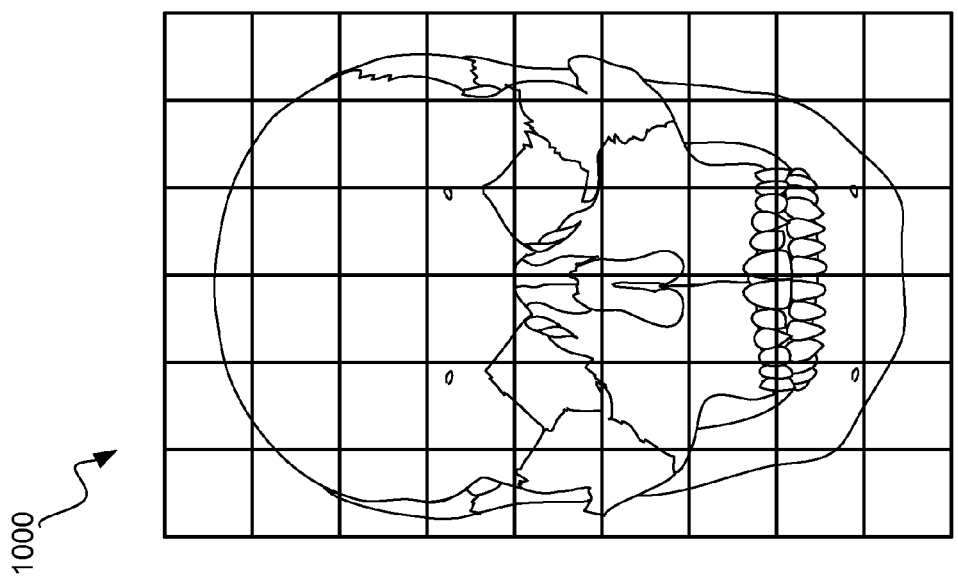
FIG. 10

| Non-midline Target Results | Cavernous Sinus | | Meckel's Cave | | Superior Optic Fissure | |
|---|---|---|---|---|---|---|
| Angles Between Instruments | Angle (degrees) | stdv | Angle (degrees) | stdv | Angle (degrees) | stdv |
| Bilateral Nasal | 15.86 | (1.88) | 14.02 | (1.93) | 16.21 | (2.23) |
| Contralateral Nasal & Ipsilateral Medial Orbit | 20.58 | (3.53) | 22.49 | (4.67) | 28.98 | (5.10) |
| Ipsilateral Nasal & Contralateral Medial Orbit | 29.74 | (4.14) | 31.83 | (4.23) | | |
| Ipsilateral Nasal & Contralateral Superior Orbit | 43.77 | (4.88) | 39.07 | (4.86) | | |
| Contralateral Nasal & Ipsilateral Lateral Orbit | 46.21 | (3.12) | 53.96 | (3.34) | 63.65 | (3.47) |
| Contralateral Medial Orbit & Ipsilateral Lateral Orbit | 58.73 | (3.04) | 59.97 | (2.59) | 76.08 | (3.42) |
| Bilateral Medial Orbit | 24.89 | (2.67) | 24.16 | (2.64) | 31.12 | (3.07) |
| Contralateral Nasal & Contralateral Medial Orbit | | | 25.27 | (5.17) | | |
| Contralateral Nasal & Ipsilateral Superior Orbit | | | 34.80 | (4.61) | | |
| Contralateral Nasal & Ipsilateral Inferior Orbit | | | 30.85 | (2.46) | | |
| Distance to Target | Distance (mm) | stdv | Distance (mm) | stdv | Distance (mm) | stdv |
| Contralateral Nasal | 99.31 | (6.16) | 98.02 | (6.40) | 85.38 | (5.78) |
| Ipsilateral Nasal | 96.26 | (5.95) | 93.93 | (6.17) | 80.75 | (5.84) |
| Contralateral Medial Orbit | 70.35 | (3.42) | 71.87 | (4.19) | 57.12 | (2.58) |
| Ipsilateral Medial Orbit | 64.29 | (3.51) | 62.74 | (4.46) | 47.84 | (2.10) |
| Contralateral Superior Orbit | 86.80 | (4.22) | 90.31 | (4.29) | 75.69 | (3.30) |
| Ipsilateral Superior Orbit | | | 73.99 | (4.54) | 60.08 | (3.33) |
| Ipsilateral Lateral Orbit | 65.10 | (4.14) | 59.65 | (4.34) | 50.46 | (4.10) |
| Contralateral Inferior Orbit | | | 84.09 | (5.09) | 71.53 | (3.80) |
| Ipsilateral Inferior Orbit | | | 65.89 | (4.80) | 54.40 | (3.90) |
| Approach Angle with respect to midsagittal plane | Angle (degrees) | stdv | Angle (degrees) | stdv | Angle (degrees) | stdv |
| Contralateral Nasal | -15.91 | (2.72) | -20.41 | (3.44) | -21.12 | (3.66) |
| Ipsilateral Nasal | -2.70 | (2.04) | -6.33 | (3.09) | -4.34 | (2.99) |
| Contralateral Medial Orbit | -24.40 | (2.85) | -30.27 | (3.41) | -33.66 | (3.09) |
| Ipsilateral Medial Orbit | 2.38 | (1.38) | 5.92 | (3.63) | 3.62 | (2.39) |
| Contralateral Superior Orbit | -32.98 | (2.35) | -37.51 | (3.06) | -41.34 | (2.58) |
| Ipsilateral Lateral Orbit | 35.17 | (2.95) | 9.26 | (2.27) | 43.41 | (2.93) |
| Contralateral Inferior Orbit | | | -40.54 | (3.30) | -45.56 | (3.62) |
| Ipsilateral Inferior Orbit | | | 10.68 | (2.93) | 18.47 | (2.97) |
| Approach Angle with respect to skull base | Angle (degrees) | stdv | Angle (degrees) | stdv | Angle (degrees) | stdv |
| Bilateral Nasal | -17.17 | (6.21) | -14.33 | (6.23) | -20.26 | (7.32) |
| Medial & Lateral Orbit | 4.57 | (3.18) | 7.85 | (4.90) | 5.37 | (3.49) |
| Superior Orbit | 15.71 | (5.52) | 20.35 | (5.95) | 20.37 | (5.72) |
| Inferior Orbit | | | 8.35 | (4.89) | 15.74 | (5.84) |

FIG. 11

| Midline Target Results | Prechiasmatic | | Postchiasmatic | | 3rd Ventricle | | Basal Cistern | | Clivus | |
|---|---|---|---|---|---|---|---|---|---|---|
| Angles Between Instruments | Angle (degrees) | stdv | Angle (degrees) | stdv | Angle (degrees) | stdv | Angle (degrees) | stdv | Angle (degrees) | stdv |
| Bilateral Nasal | 14.69 | (1.89) | 13.20 | (1.72) | 12.50 | (1.69) | 13.03 | (1.72) | 12.60 | (1.80) |
| Nasal and Opposite Medial Orbit | 23.31 | (3.39) | 22.66 | (3.56) | 22.34 | (3.47) | 26.05 | (3.68) | 26.27 | (4.35) |
| Nasal and Opposite Superior Orbit | 43.91 | (4.62) | 41.37 | (3.63) | | | | | | |
| Bilateral Medial Orbit | 26.63 | (3.17) | 24.83 | (2.50) | 25.09 | (3.09) | 22.21 | (3.22) | 19.86 | (2.87) |
| Bilateral Superior Orbit | | | 46.03 | (3.62) | | | | | | |
| Nasal and Opposite Inferior Orbit | | | | | 44.68 | (4.73) | 45.90 | (2.65) | 43.01 | (3.86) |
| Distances to Target | Distance (mm) | stdv | Distance (mm) | stdv | Distance (mm) | stdv | Distance (mm) | stdv | Distance (mm) | stdv |
| Nasal | 93.23 | (5.61) | 103.74 | (7.04) | 109.59 | (9.92) | 104.93 | (6.09) | 108.71 | (9.10) |
| Medial Orbit | 58.95 | (2.36) | 70.38 | (3.57) | 74.54 | (6.70) | 76.50 | (2.45) | 86.03 | (4.98) |
| Superior Orbit | 79.41 | (2.39) | 82.41 | (5.67) | 84.63 | (9.37) | 91.72 | (3.18) | 102.86 | (6.38) |
| Inferior Orbit | | | | | 85.66 | (9.02) | 83.85 | (4.06) | 89.49 | (5.47) |
| Approach Angle with respect to midsagittal plane | Angle (degrees) | stdv | Angle (degrees) | stdv | Angle (degrees) | stdv | Angle (degrees) | stdv | Angle (degrees) | stdv |
| Nasal | 8.01 | (1.39) | 7.14 | (1.28) | 7.01 | (3.29) | 6.85 | (2.77) | 6.20 | (2.51) |
| Medial Orbit | 14.68 | (1.73) | 13.50 | (1.40) | 12.28 | (2.97) | 11.35 | (2.14) | 10.46 | (2.12) |
| Lateral Orbit | 47.93 | (2.21) | | | 41.50 | (5.54) | 38.84 | (2.45) | 36.10 | (3.46) |
| Superior Orbit | 26.48 | (1.53) | 23.29 | (1.78) | 22.91 | (3.87) | 21.47 | (1.85) | 20.03 | (1.85) |
| Inferior Orbit | | | | | 25.27 | (4.04) | 23.50 | (2.34) | 21.76 | (3.65) |
| Approach Angle with respect to skull base | Angle (degrees) | stdv | Angle (degrees) | stdv | Angle (degrees) | stdv | Angle (degrees) | stdv | Angle (degrees) | stdv |
| Nasal | -22.30 | (6.02) | -21.25 | (6.78) | -24.71 | (6.50) | -11.52 | (5.75) | -4.74 | (5.02) |
| Medial Orbit | 3.47 | (4.17) | 5.90 | (4.62) | 11.78 | (7.43) | 8.31 | (5.41) | 18.73 | (4.30) |
| Lateral Orbit | 8.20 | (4.56) | | | 15.40 | (6.16) | 8.40 | (6.09) | 20.31 | (4.88) |
| Superior Orbit | 11.66 | (5.93) | 8.39 | (6.22) | 5.03 | (4.86) | 18.31 | (8.02) | 27.25 | (4.99) |
| Inferior Orbit | | | | | 29.18 | (7.44) | 6.53 | (4.25) | 7.27 | (4.43) |

METHODS AND SYSTEMS FOR SELECTING SURGICAL APPROACHES

RELATED APPLICATIONS

This application is a U.S. national phase of International Application No. PCT/US2013/075115, filed on Dec. 13, 2013, which claims priority to U.S. Provisional Application No. 61/737,008, filed Dec. 13, 2012, both of which are incorporated by reference herein in their entirety.

BACKGROUND

Unless otherwise indicated herein, the materials described in this section are not prior art to the claims in this application and are not admitted to be prior art by inclusion in this section.

Surgical planning may involve identifying a surgical target or target region, and then selecting a surgical pathway to reach that surgical target. Selection of a particular surgical pathway is often based upon the access that the surgical pathway provides to the surgical target in view of the nearby anatomy. Better access to the surgical target may lead to a better surgical outcome.

However, better access to a surgical target is not the sole determinant of a successful surgical outcome. Another goal of surgical planning is to reduce collateral damage to the nearby anatomy. Collateral damage may include pathway trauma, which refers to damage incurred by dissection performed to reach the surgical target. In addition, collateral damage may include target trauma, or damage to healthy tissue that is adjacent to the surgical target that occurs when the surgical target is manipulated. The extent of target trauma is often dictated by the pathology of the surgical target. In contrast, pathway trauma might be reduced by appropriate selection of surgical pathways.

Selection of surgical pathways may begin with choosing a surgical portal, or opening, in the anatomy that is being operated upon. For example, in skull base surgery, transnasal portals have been identified that may form the entry point of surgical pathways into the skull base. Use of transnasal portals as part of the surgical pathway has led to reduced pathway trauma in some circumstances.

At the same time, rapid advances in many fields of surgery have led to the identification of new surgical pathways. Additional surgical pathways into the skull base as well as new surgical pathways to other anatomical features are likely to be identified in the future. By extension, the identification of new surgical portals has led to successful surgeries using multiple portals and pathways. Combined surgical approaches have significant potential to reduce collateral damage to healthy tissue.

However, the number of possible surgical pathways and combinations thereof is extensive. Moreover, because of the inconsistent and unpredictable nature of target pathologies, selection of an appropriate pathway or combination of pathways is often unintuitive. Therefore, a systematic approach to comparing, evaluating, and selecting between surgical approaches may improve surgical outcomes.

SUMMARY

Described herein are methods and systems for surgical planning. The methods and systems may be employed during surgical planning to assist in selection of one or more surgical approaches. Such methods and systems may involve determining surgical-approach characteristics and surgical-pathway characteristics that can be used to rank various surgical approaches. These surgical approach rankings can aid in selecting an appropriate surgical pathway or combination of pathways for a given surgical target. A representation of the selected surgical pathway or combination of pathways may be provided via one or more output device that may improve access to the surgical target and reduce collateral damage, among other potential benefits.

In one aspect, a computer-implemented method is provided. The method may involve: (1) receiving data indicating (a) one or more surgical target regions and (b) one or more surgical portals; (2) determining a plurality of surgical pathways, wherein each surgical pathway in the plurality of surgical pathways comprises (a) a respective surgical target region of the one or more surgical target regions and (b) a respective surgical portal of the one or more surgical portals; (3) determining a plurality of surgical approaches, wherein each surgical approach in the plurality of surgical approaches comprises at least a first determined surgical pathway; (4) for each surgical approach in the plurality of surgical approaches, determining at least one approach characteristic, for each determined surgical pathway in the respective surgical approach, determining at least one pathway characteristic, and determining a surgical-approach ranking based on the determined at least one approach characteristic and the determined at least one pathway characteristic; (5) selecting a subset of the plurality of surgical approaches based on the determined surgical approach rankings; and (6) causing an output device to provide a representation of the selected subset of the plurality of surgical approaches.

In another aspect, a computing system is provided. The computing system may include: (A) an output device; (B) a physical, non-transitory computer readable medium; and (C) program instructions stored on the physical computer readable medium and executable by at least one processor to cause the computing system to: (1) receive data indicating (a) one or more surgical target regions and (b) one or more surgical portals; (2) determine a plurality of surgical pathways, wherein each surgical pathway in the plurality of surgical pathways comprises (a) a respective surgical target region of the one or more surgical target regions and (b) a respective surgical portal of the one or more surgical portals; (3) determine a plurality of surgical approaches, wherein each surgical approach in the plurality of surgical approaches comprises at least a first determined surgical pathway; (4) for each surgical approach in the plurality of surgical approaches, determine at least one approach characteristic, for each determined surgical pathway in the respective surgical approach, determine at least one pathway characteristic, and determine a surgical-approach ranking based on the determined at least one approach characteristic and the determined at least one pathway characteristic; (5) select a subset of the plurality of surgical approaches based on the determined surgical approach rankings; and (6) cause an output device to provide a representation of the selected subset of the plurality of surgical approaches.

In another aspect, a physical, non-transitory computer-readable medium is provided. The physical computer-readable medium may include instructions that are executable by a computing system to cause the computing system to perform functions. The functions include: (1) receiving data indicating (a) one or more surgical target regions and (b) one or more surgical portals; (2) determining a plurality of surgical pathways, wherein each surgical pathway in the plurality of surgical pathways comprises (a) a respective surgical target region of the one or more surgical target regions and (b) a respective surgical portal of the one or more surgical portals; (3) determining a plurality of surgical approaches, wherein each surgical approach in the plurality of surgical approaches comprises at least a first determined surgical pathway; (4) for each surgical approach in the plurality of surgical approaches, determining at least one approach characteristic, for each determined surgical pathway in the respective surgical approach, determining at least one pathway characteristic, and determining a surgical-approach ranking based on the determined at least one approach characteristic and the determined at least one pathway characteristic; (5) selecting a subset of the plurality of surgical approaches based on the determined surgical approach rankings: and (6) causing an output device to provide a representation of the selected subset of the plurality of surgical approaches.

In another aspect, another computer-implemented method is provided. The method may involve: (1) receiving data for a patient indicating (a) one or more surgical target regions within the patient and (b) one or more surgical portals of the patient; (2) determining a plurality of surgical pathways, wherein each surgical pathway in the plurality of surgical pathways comprises (a) a respective surgical target region of the one or more surgical target regions and (b) a respective surgical portal of the one or more surgical portals; (3) determining a plurality of surgical approaches, wherein each surgical approach in the plurality of surgical approaches comprises at least a first determined surgical pathway; (4) for each surgical approach in the plurality of surgical approaches, determining at least one approach characteristic, for each determined surgical pathway in the respective surgical approach, determining at least one pathway characteristic, and determining a surgical-approach ranking based on the determined at least one approach characteristic and the determined at least one pathway characteristic; (5) selecting a subset of the plurality of surgical approaches based on the determined surgical approach rankings; and (6) causing an output device to provide a representation of the selected subset of the plurality of surgical approaches.

In another aspect, another computing system is provided. The computing system may include: (A) an output device; (B) a physical, non-transitory computer readable medium; and (C) program instructions stored on the physical computer readable medium and executable by at least one processor to cause the computing system to: (1) receive data for a patient indicating (a) one or more surgical target regions within the patient and (b) one or more surgical portals of the patient; (2) determine a plurality of surgical pathways, wherein each surgical pathway in the plurality of surgical pathways comprises (a) a respective surgical target region of the one or more surgical target regions and (b) a respective surgical portal of the one or more surgical portals; (3) determine a plurality of surgical approaches, wherein each surgical approach in the plurality of surgical approaches comprises at least a first determined surgical pathway: (4) for each surgical approach in the plurality of surgical approaches, determine at least one approach characteristic, for each determined surgical pathway in the respective surgical approach, determine at least one pathway characteristic, and determine a surgical-approach ranking based on the determined at least one approach characteristic and the determined at least one pathway characteristic; (5) select a subset of the plurality of surgical approaches based on the determined surgical approach rankings; and (6) cause an output device to provide a representation of the selected subset of the plurality of surgical approaches.

In another aspect, another physical, non-transitory computer-readable medium is provided. The physical computer-readable medium may include instructions that are executable by a computing system to cause the computing system to perform functions. The functions include: (1) receiving data for a patient indicating (a) one or more surgical target regions within the patient and (b) one or more surgical portals of the patient; (2) determining a plurality of surgical pathways, wherein each surgical pathway in the plurality of surgical pathways comprises (a) a respective surgical target region of the one or more surgical target regions and (b) a respective surgical portal of the one or more surgical portals; (3) determining a plurality of surgical approaches, wherein each surgical approach in the plurality of surgical approaches comprises at least a first determined surgical pathway; (4) for each surgical approach in the plurality of surgical approaches, determining at least one approach characteristic, for each determined surgical pathway in the respective surgical approach, determining at least one pathway characteristic, and determining a surgical-approach ranking based on the determined at least one approach characteristic and the determined at least one pathway characteristic; (5) selecting a subset of the plurality of surgical approaches based on the determined surgical approach rankings; and (6) causing an output device to provide a representation of the selected subset of the plurality of surgical approaches.

These as well as other aspects, advantages, and alternatives, will become apparent to those of ordinary skill in the art by reading the following detailed description, with reference where appropriate to the accompanying drawings.

BRIEF DESCRIPTION OF THE FIGURES

FIG. 4 shows an illustrative three-dimensional model of a human skull.

FIG. 5 shows illustrative approach vectors indicating surgical portals within an illustrative three-dimensional model of a human skull.

FIG. 10 shows an illustrative modular representation of a model of a human skull.

FIG. 11 shows a table of determined approach and pathway characteristics for non-midline surgical target regions in the study of fourteen subjects.

FIG. 12 shows a table of determined approach and pathway characteristics for midline surgical target regions in the study of fourteen subjects.

FIG. 15 shows a table of determined approach and pathway characteristics, and measured approach and pathway characteristics, on four cadavers.

DETAILED DESCRIPTION

In the following detailed description, reference is made to the accompanying figures, which form a part thereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the spirit or scope of the subject matter presented herein. It will be readily understood that aspects of the present disclosure, as generally described herein, and illustrated in the figures, can be arranged, substituted, combined, separated, and/or designed in a wide variety of different configurations, all of which are explicitly contemplated herein.

1. EXAMPLE ARCHITECTURE

Figure 1:
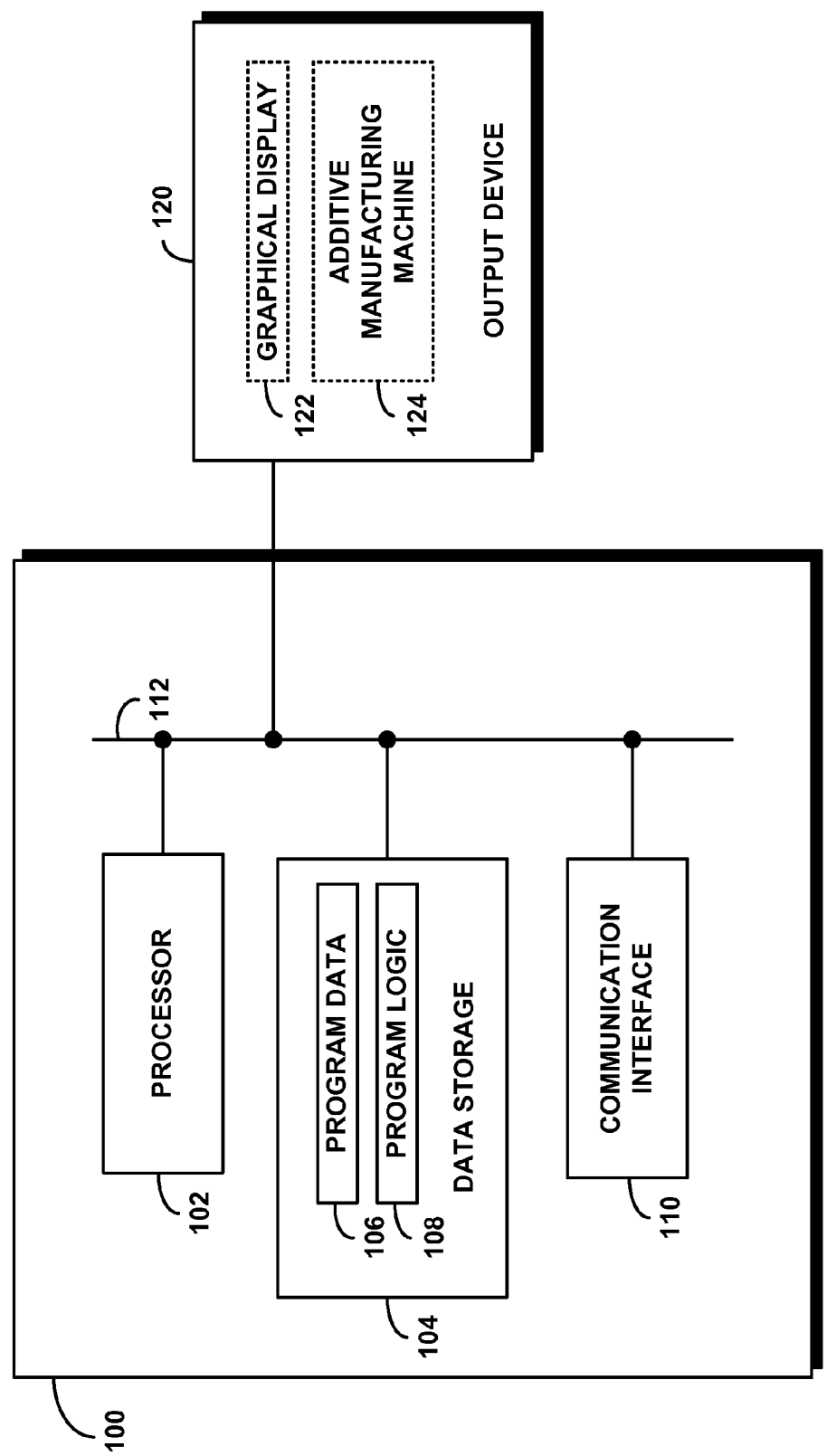
FIG. 1 shows a simplified block diagram of a computing system, in accordance with an example embodiment.

FIG. 1 shows a simplified block diagram of an example computing system 100 in which the present method can be implemented. It should be understood that this and other arrangements described herein are set forth only as examples. Those skilled in the art will appreciate that other arrangements and elements (e.g., machines, interfaces, functions, orders, and groupings of functions, etc.) can be used instead and that some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. And various functions described herein may be carried out by a processor executing instructions stored in memory.

As shown in FIG. 1, computing system 100 may include processor 102, data storage 104, and communication interface 110, all linked together via system bus, network, or other connection mechanism 112.

Processor 102 may include one or more general purpose microprocessors and/or one or more dedicated signal processors and may be integrated in whole or in part with communication interface 110. Data storage 104 may include memory and/or other storage components, such as optical, magnetic, organic or other memory disc storage, which can be volatile and/or non-volatile, internal and/or external, and integrated in whole or in part with processor 102. Data storage 104 may be arranged to contain (i) program data 106 and (ii) program logic 108. Although these components are described herein as separate data storage elements, the elements could just as well be physically integrated together or distributed in various other ways. For example, program data 106 may be maintained in data storage 104 separate from program logic 108, for easy updating and reference by program logic 108.

Communication interface 110 typically functions to communicatively couple computing system 100 to networks. As such, communication interface 110 may include a wired (e.g., Ethernet) and/or wireless (e.g., Wi-Fi) packet-data interface, for communicating with other devices, entities, and/or networks. Computing system 100 may also include multiple interfaces 110, such as one through which computing system 100 sends communication, and one through which computing system 100 receives communication.

Computing system 100 may also include, or may be otherwise communicatively coupled to, output device 120. Output device 120 may include one or more elements for communicating outputs, for example, one or more graphical displays 122 and/or a speaker. In operation, user interface 120 may be configured to display a graphical user interface (GUI) via graphical display 122, corresponding to use of such a GUI. Output device 120 may additionally or alternatively include a manufacturing machine, such as a printer. In some embodiments, the manufacturing machine may be an additive manufacturing machine 124, also known as a three-dimensional printer. In operation, additive manufacturing machine 124 may be configured to provide one or more three-dimensional representations of the human body, parts thereof, or elements associated with surgery from data representing a three-dimensional model.

Figure 2:
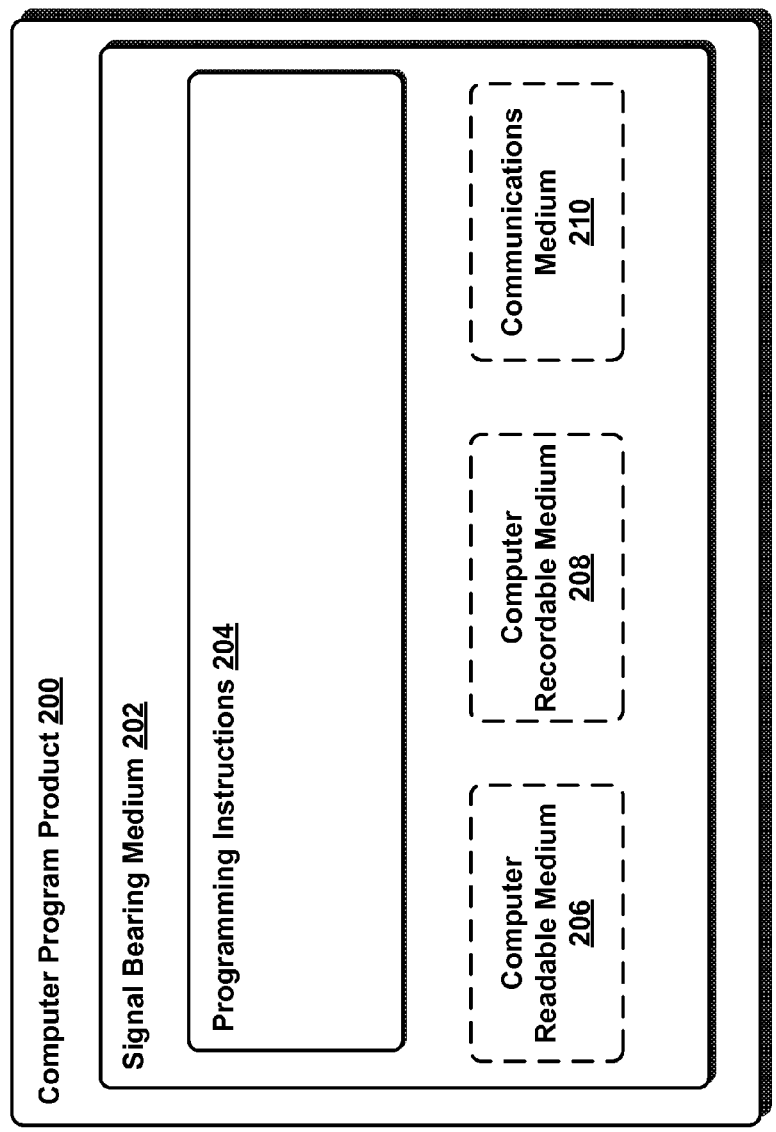
FIG. 2 shows an illustrative computer-readable medium, in accordance with an example embodiment.

As noted above, in some embodiments, the disclosed methods may be implemented by computer program instructions encoded on a physical, and/or non-transitory, computer-readable storage media in a machine-readable format, or on other non-transitory media or articles of manufacture. FIG. 2 is a schematic illustrating a conceptual partial view of an example computer program product that includes a computer program for executing a computer process on a computing system, arranged according to at least some embodiments presented herein.

In one embodiment, the example computer program product 200 is provided using a signal bearing medium 202. The signal bearing medium 202 may include one or more programming instructions 204 that, when executed by one or more processors may provide functionality or portions of the functionality described herein. In some examples, the signal bearing medium 202 may encompass a computer-readable medium 206, such as, but not limited to, a hard disk drive, a Compact Disc (CD), a Digital Video Disk (DVD), a digital tape, memory, etc. In some implementations, the signal bearing medium 202 may encompass a computer-recordable medium 208, such as, but not limited to, memory, read/write (R/W) CDs, R/W DVDs, etc. In some implementations, the signal bearing medium 202 may encompass a communications medium 210, such as, but not limited to, a digital and/or an analog communication medium (e.g., a fiber optic cable, a waveguide, a wired communications link, a wireless communication link, etc.). Thus, for example, the signal bearing medium 202 may be conveyed by a wireless form of the communications medium 210. It should be understood, however, that computer-readable medium 206, computer recordable medium 208, and communications medium 210 as contemplated herein are distinct mediums and that, in any event, computer-readable medium 208 is a physical, non-transitory, computer-readable medium.

The one or more programming instructions 204 may be, for example, computer executable and/or logic implemented instructions. In some examples, a computing system such as the computing system 100 of FIG. 1 may be configured to provide various operations, functions, or actions in response to the programming instructions 204 conveyed to the computing system 100 by one or more of the computer readable medium 206, the computer recordable medium 208, and/or the communications medium 210.

2. EXAMPLE METHOD

Figure 3A:
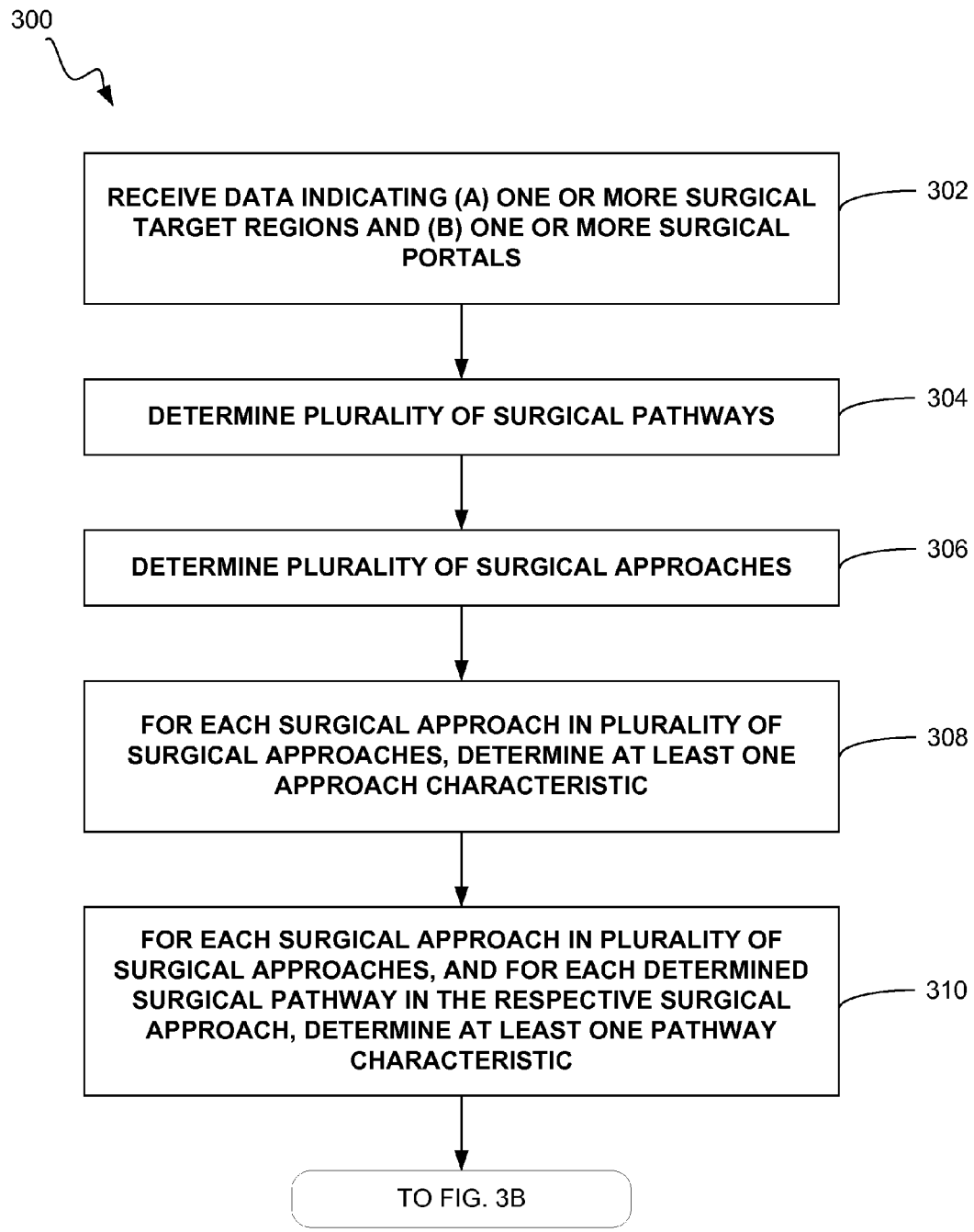
FIG. 3A shows a first part of an illustrative method for selecting surgical approaches.
Figure 3B:
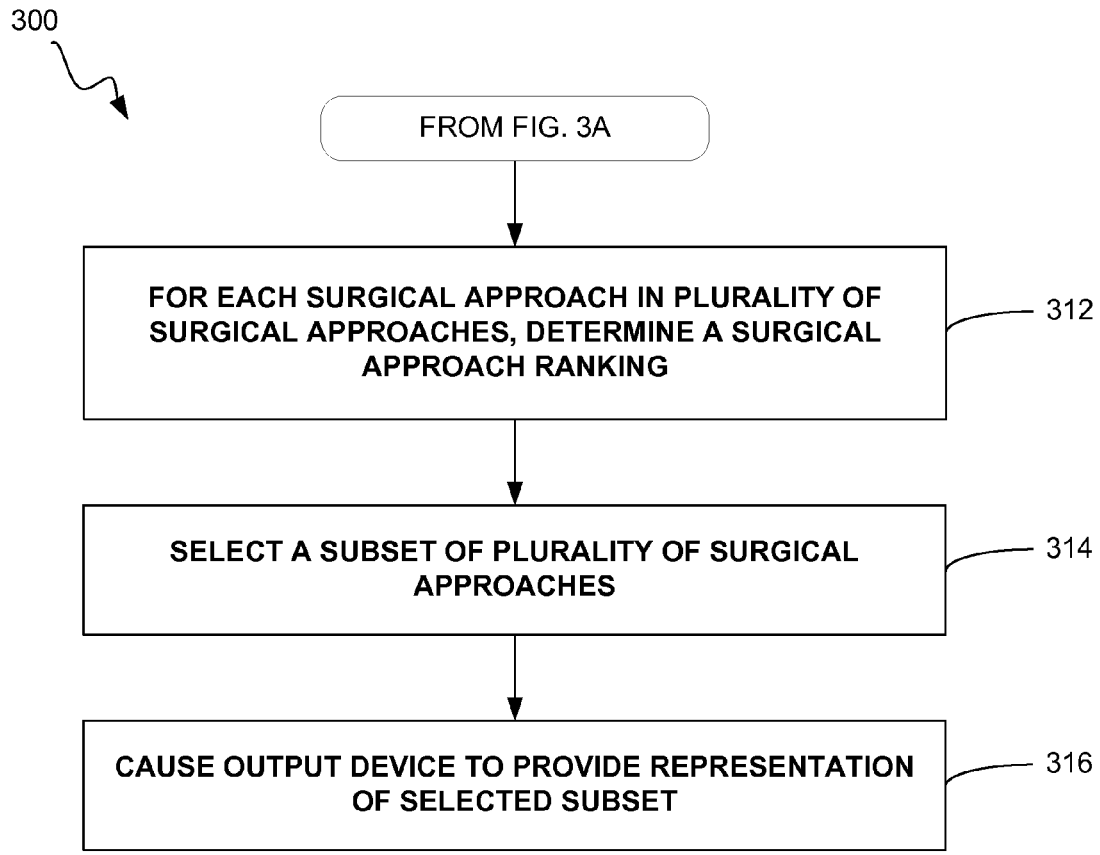
FIG. 3B shows a second part of the illustrative method for selecting surgical approaches.

FIGS. 3A and 3B show a flowchart depicting functions that can be carried out in accordance with at least one embodiment of an example method. As shown in FIG. 3A, method 300 begins at block 302 with a computing system receiving data indicating (a) one or more surgical target regions and (b) one or more surgical portals. At block 304, the computing system determines a plurality of surgical pathways, where each surgical pathway in the plurality of surgical pathways includes (a) a respective surgical target region of the one or more surgical target regions and (b) a respective surgical portal of the one or more surgical portals. At block 306, the computing system determines a plurality of surgical approaches, where each surgical approach in the plurality of surgical approaches comprises at least a first determined surgical pathway. At block 308, for each surgical approach in the plurality of surgical approaches, the computing system determines at least one approach characteristic. At block 310, for each surgical approach in the plurality of surgical approaches, the computing system determines, for each determined surgical pathway in the respective surgical approach, at least one pathway characteristic. Turning to FIG. 3B, method 300 continues at block 312, where, for each surgical approach in the plurality of surgical approaches, the computing system determines a surgical-approach ranking based on the determined at least one approach characteristic and the determined at least one pathway characteristic. At block 314, the computing system selects a subset of the plurality of surgical approaches based on the determined surgical approach rankings. At block 316, the computing system causes an output device to provide a representation of the selected subset of the plurality of surgical approaches.

In some implementations, method 300 may be carried out entirely, or in part, by computing system 100. Other suitable computing systems may be used as well.

a. Receive Data Indicating (A) One or More Surgical Target Regions and (B) One or More Surgical Portals At block 302, the computing system receives data indicating (a) one or more surgical target regions and (b) one or more surgical portals. For example, computing system 100 in FIG. 1 may receive the data over system bus, network, or other connection mechanism 112. In some embodiments, the computer system may receive the imaging data from a medical imaging machine, such as a magnetic resonance imaging (MRI) machine, a positron emission tomography (PET) machine, or a computed tomography (CT) machine. In other embodiments, the computing system may receive the imaging data from a computing device via a network. In some embodiments, the computing system may receive the imaging data via a transfer from a data storage device, such as a hard disk drive or a USB flash drive. In other embodiments, the computing system may receive the imaging data via a transfer from a data storage medium, such as a CD-ROM disk. Many other examples are possible as well.

The data indicating the one or more surgical target regions may include data defining the one or more surgical target regions as volumes within a model. In planning for, preparing for, or performing a surgery, data representing a model of one or more anatomical structures may be provided to a computing system. In some embodiments, the data may also define a three-dimensional (3-d) coordinate system. Each of the one or more anatomical structures may include data points that define a respective volume within the three-dimensional coordinate system for each of the one or more anatomical structures. The data points that define volumes in the model may indicate specific sets of coordinates within the 3-d coordinate system, such as one or more (x,y,z) coordinates.

In some embodiments, each data point in the model may represent a voxel, or volume element. In such embodiments, each coordinate in the 3-d coordinate system may reference a specific voxel. Each voxel may represent a physical volume.

The anatomical structures may relate to the surgery. For example, the anatomical structures may neighbor a region that may be operated on during surgery. In some embodiments, anatomical structures not related to the surgery may also be provided in the model. Such unrelated anatomical structures may assist in visualization and orientation, among other benefits.

The data representing the model may be provided via one or more medical images that show one or more images of the human body (or a part thereof). Such medical images may be created using one or more of a variety of medical imaging techniques, such as magnetic resonance imaging MRI, PET, or CT. Other types of medical images are contemplated as well, such as ultrasound, tactile imaging, or photoacoustic imaging, among other possibilities.

Such medical images may provide 3-d representations of the human body, or the part thereof that has been imaged. The 3-d representations may be translated into the model of the one or more anatomical structures. A 3-d representation may be provided from a set of medical images, known as a scan. In some embodiments, a three-dimensional (3-d) medical image may be provided by combining multiple two-dimensional (2-d) images as layers to form a three-dimensional image. In other embodiments, the medical imaging machine produces a three-dimensional medical image.

In some embodiments, the model may indicate a representative human body or part thereof. Such a representative human body or part thereof may be provided by normalizing data from multiple medical images of different patients to form the representative human body or part thereof. In other embodiments, the model may indicate a patient's body or part thereof.

FIG. 4 depicts an illustrative model 400. Model 400 is a three-dimensional representation of a human skull. In FIG. 4, the three-dimensional model is depicted as two-dimensional representations presented as front and side views of the three-dimensional model, as shown. Model 400 may be provided by normalizing the data of medical scans of the skulls from multiple subjects having normal skull anatomy. It should be understood that the particular model shown in FIG. 4 is set forth for purposes of example and explanation only. Other examples of models exist, and any such models may be within the scope of the example method disclosed herein. For example, the model might include a three-dimensional representation of a human abdomen. The model shown in FIG. 4 should not be taken to be limiting.

The one or more surgical target regions may include a target pathology such as a lesion. In some circumstances, the target pathology may be located within an anatomical location. Such an anatomical location may include a cavity within the body. Additionally or alternatively, the anatomical location may include an anatomical feature. The surgical target region may define a three-dimensional volume within the three-dimensional coordinate system. For example, the surgical target region may include a brain lesion within the right Meckel's cave, among many other possible examples. Conversely, the surgical target region may include one or more anatomical features that are not currently affected by pathology, but for which surgical manipulation is suggested for other reasons.

In some embodiments, such a surgical target region may be later manipulated by one or more surgical instruments. In the case where the surgical target region includes a target pathology, manipulation of the surgical target region may be performed to remove the pathology, for example, to remove a lesion. Manipulation of the surgical target region for removal of the lesion may include various techniques such as ablation. However, manipulation of the surgical target region is not necessary to the method described herein.

In some embodiments, the one or more surgical target regions may include a surgical margin. The surgical margin may define a region that fully or partially surrounds a target pathology that may be excised during the surgery. For example, the surgical margin may be an area of tumor free tissue surrounding a tumor that may be removed along with the tumor.

For example, the one or more surgical target regions may be located within one or more of the following surgical target locations: pre-chiasmatic, post-chiasmatic, right cavernous sinus, left cavernous sinus, right Meckel's Cave, left Meckel's Cave, right superior orbital fissure, left superior orbital fissure, third ventricle extension, basal cistern extension, and clivus. The aforementioned example surgical target locations are located within the skull. However, one having skill in the art will appreciate that many examples of surgical target regions in locations other than the skull are possible. Moreover, surgical target regions at additional locations within the skull are possible as well. For example, surgical target regions within the chest or abdomen are possible.

The data indicating the one or more surgical portals may include data defining the one or more surgical portals as volumes within the model. The volumes may include data points at a specific set of coordinates within the 3-d coordinate system, such as one or more (x,y,z) coordinates. The surgical portals may be entry points into the human body. During surgery, surgical instruments may be inserted into the surgical portal. Some surgical portals may be openings, or orifices, into the human body that provide entry points that ease access into the body. The transnasal portal is an example of an opening that provides access into the skull, a part of the body. Other surgical portals may be entry points that ease access into the skull when some part of the human anatomy is displaced. For example, the transorbital and supraorbital portals provide access into the skull when the eye is displaced. Certain surgical portals may be chosen for a particular surgery based on the relative location of the chosen surgical portal to the surgical target region.

For example, the one or more surgical portals may include one or more of the following surgical portals: right transnasal, left transnasal, right superior lid crease (superior orbit wall), right lateral retrocanthal (lateral orbit wall), right transconjuctival (inferior orbit wall), right precaruncular (medial orbital wall), left superior lid crease (superior orbital wall), left lateral retrocanthal (lateral orbit wall), left transconjunctival (inferior orbit wall), and left precaruncular (medial orbital wall). The aforementioned example surgical portals are located within the skull. However, one having skill in the art will appreciate that many examples of surgical portals in locations other than the skull are possible. For example, the surgical portals may be located on the exterior of the chest or abdomen. Or, as another example, the surgical portals may include the anus. Moreover, surgical portals at additional locations within the skull are possible as well.

FIG. 5 depicts an illustrative model 500 that shows example surgical portals that are indicated by approach vectors 502, 504, 506, 508, and 510. The approach vectors may aid in visualization of the surgical portals. Each of approach vectors 502, 504, 506, 508, and 510 indicates a surgical portal at one end of the respective approach vector. Approach vector 502 indicates the left precaruncular portal. Approach vector 504 indicates the left superior lid crease portal. Approach vector 506 indicates the left lateral retrocanthal portal. Approach vector 508 indicates the left transconjunctival portal. And, approach vector 510 indicates the left transnasal portal. The approach vectors indicating surgical portals are provide for example only and should not be taken as limiting. Other surgical portals exist but are not shown in this model.

i. Receiving Data in a Study of Fourteen Subjects

In the study, a model of skull base anatomy was provided by normalizing data from 14 CT scans of normal skull base anatomy from 14 patients including eight males and six females ranging in age from 23 to 65. The pituitary gland, internal carotid arteries, cavernous sinuses, optic nerves, and chiasm were defined as three-dimensional volumes in the model.

Eleven surgical target regions were identified that include: pre-chiasmatic, post-chiasmatic, right cavernous sinus, left cavernous sinus, right Meckel's Cave, left Meckel's Cave, right superior orbital fissure, left superior orbital fissure, third ventricle extension, basal cistern extension, and clivus.

Ten surgical portals that may provide access to the identified surgical target regions were identified that include: right transnasal, left transnasal, right superior lid crease (superior orbit wall), right lateral retrocanthal (lateral orbit wall), right transconjuctival (inferior orbit wall), right precaruncular (medial orbital wall), left superior lid crease (superior orbital wall), left lateral retrocanthal (lateral orbit wall), left transconjunctival (inferior orbital wall), and left precaruncular (medial orbital wall). The ten surgical portals were defined at the entry point into the skin or nasal vestibule. The transnasal entry points were defined lateral to the nasal vestibule as limited by the pyriform aperture. The transorbital portals were defined at the four quadrants of the orbit wall, as noted above as the superior lid crease, lateral retrocanthal, transconjuctival, and precaruncular.

b. Determine Plurality of Surgical Pathways

At block 304, the computing system determines a plurality of surgical pathways, where each surgical pathway in the plurality of surgical pathways includes (a) a respective surgical target region of the one or more surgical target regions and (b) a respective surgical portal of the one or more surgical portals. In practice, for each surgical pathway in the plurality of determined surgical pathways, surgical instruments may be inserted into the surgical portal and through the surgical pathway, in order to access the surgical target region. However, insertion of surgical instruments is not a necessary aspect of the method described herein. The plurality of surgical pathways may include various combinations of the one or more surgical portals and the one or more surgical target regions.

Determining the plurality of surgical pathways may include, for each surgical pathway in the plurality of surgical pathways, determining the data points within the model that define a volume representing the respective surgical pathway that extends from the respective surgical portal to the respective surgical target region. Along the length of each surgical pathway, the area of the cross section of the surgical pathway may be increased or decreased to reflect the available space within the body allowed by neighboring anatomical structures that have been provided in the model. For example, where the surgical pathway includes a transorbital portal, the surgical pathway may narrow at the point along the surgical pathway where the surgical pathway passes the eye, such that the cross section of the volume may narrow at the point along the surgical pathway where the surgical pathway passes the eye.

As one with skill in the art will appreciate, in some circumstances, tissue may be removed from a surgical pathway to create or widen the pathway for the passage of surgical instruments, among other possible manipulations of the surgical pathway. In some embodiments, removal of tissue may be performed in accordance with a known surgical technique. Each respective surgical pathway may be represented as the surgical pathway appears before or after the removal of tissue to alter the surgical pathway. In further embodiments, the model may assist in planning the removal of tissue to alter the surgical pathway by representing the surgical pathway before and/or after the removal of tissue.

In some embodiments, the plurality of surgical pathways may include possible combinations of the one or more surgical portals and the one or more surgical target regions. For example, if the one or more surgical portals include three surgical portals (labelled for identification as A, B, & C) and one surgical target region (z), three surgical pathways may be determined (A-z, B-z, & C-z). Or, if there are twenty surgical portals and three surgical target regions, sixty surgical pathways may be determined. In other embodiments, fewer than the total number of possible combinations may be determined.

Figure 6:
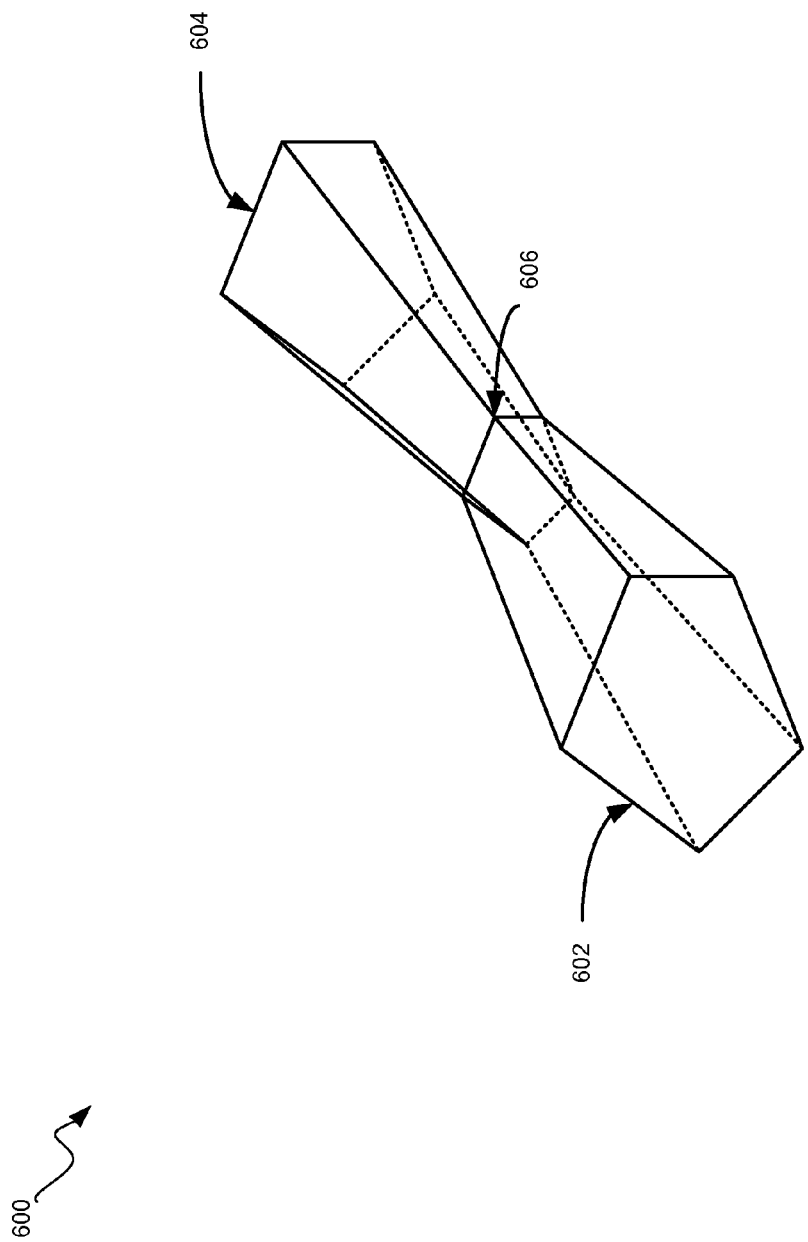
FIG. 6 shows an illustrative representation of aspects of a surgical pathway.

FIG. 6 depicts an illustration of a surgical pathway 600 that can be understood to extend from a surgical portal to a surgical target region. FIG. 6 is a simplified representation for the purpose of example and illustration. Surgical pathway 600 is represented by three polygons having five vertices each that form a three-dimensional volume, as shown. One polygon 602 represents the extent of the surgical portal. The second polygon 604 represents the extent of the surgical target region. The third polygon 606 represents a narrow point in the surgical pathway. Additional or fewer polygons having more or less vertices may be used to represent other surgical pathways. One having skill in the art will appreciate that other techniques for modeling the surgical pathway are possible as well.

c. Determine a Plurality of Surgical Approaches

At block 306, the computing system determines a plurality of surgical approaches, where each surgical approach in the plurality of surgical approaches includes at least a first determined surgical pathway. In some embodiments, each surgical approach in the plurality of surgical approaches may include a second determined surgical pathway. In other embodiments, each surgical approach in the plurality of surgical approaches may include a plurality of determined surgical pathways.

Determining each surgical approach in the plurality of surgical approaches may involve choosing an appropriate surgical pathway or combination of surgical pathways for a particular surgery. In some embodiments, determining each surgical approach in the plurality of surgical approaches may involve choosing one or more surgical pathways through which one or more surgical instruments can access the surgical target region for appropriate action in relation to the surgical target region. For example, the particular surgery may involve use of an endoscope for viewing the surgical target region and an instrument for ablation of the surgical target region. In such an example, each surgical approach in the determined plurality of surgical approaches may include a surgical pathway that may accommodate the endoscope and a surgical pathway that may accommodate the instrument for ablation.

In some embodiments, choosing an appropriate surgical pathway or combination of surgical pathways for a particular surgery may be based on parameters related to the surgery received by the computing system. In some embodiments, the parameters related to the surgery may be stored in a predetermined table. In other embodiments, the parameters related to the surgery may be received as user input from a user, such as a surgeon.

In some circumstances, there may be multiple appropriate surgical pathways or combinations thereof that may be appropriate for the particular surgery. Therefore, a plurality of surgical approaches may be determined, where each surgical approach includes a surgical pathway or combination of surgical pathways that may be appropriate for the particular surgery.

i. Determining Surgical Approaches in the Study of Fourteen Subjects

In the study, the left cavernous sinus was chosen as the surgical target region. Two surgical instruments were assumed: therefore each surgical approach included two surgical pathways. Eight surgical approaches were determined. The determined surgical approaches are in Table 1, below. Since the target for each surgical pathway is the same, the surgical pathways are identified by their surgical portal.

TABLE 1

Determined Surgical Approaches

| Surgical Approach To Left Cavernous Sinus | Portal of First Determined Surgical Pathway | Portal of Second Determined Surgical Pathway |
| --- | --- | --- |
| 1 | Left transnanal | Right transnasal |
| 2 | Right transnasal | Right medial orbit |
| 3 | Left transnanal | Right medial orbit |
| 4 | Right transnasal | Right superior orbit |
| 5 | Left transnanal | Right superior orbit |
| 6 | Right transnasal | Left lateral orbit |
| 7 | Right medial orbit | Left lateral orbit |
| 8 | Right medial orbit | Left medial orbit | d. Determine at Least One Approach Characteristic

At block 308, for each determined surgical approach in the plurality of surgical approaches, the computing system determines at least one approach characteristic. The approach characteristic may be a quantitative quality that may cause a particular surgical approach to be more or less appropriate for the particular surgery. In some embodiments, the approach characteristic may indicate a relationship between two or more surgical pathways. More particularly, the combination of surgical pathways in the surgical approach may lead to more desirable or less desirable results.

In some embodiments, one or more surgical approaches in the plurality of surgical approaches may further include a second determined surgical pathway. In such embodiments, the at least one determined approach characteristic may include an angulation between the first determined surgical pathway and the second determined surgical pathway. An angulation may be a characteristic that indicates an angle. As noted above, the surgical pathways may be arranged to permit the insertion of surgical instruments. Where two surgical instruments are used, a relatively small angle, for example, less than 15°, may result in a relatively small working distance between the two surgical instruments if both surgical instruments are each inserted into a respective determined surgical pathway to act in relation to the surgical target region. In some circumstances, a relatively small angle may result in a working distance that is inappropriately small, such that collisions between the two surgical instruments may result when the surgical instruments are inserted into the surgical pathway.

In some embodiments, the angle between the first determined surgical pathway and the second determined surgical pathway may be calculated using the linear algebraic relationship between two vectors in 3-d space. In such embodiments, the first determined surgical pathway and the second determined surgical pathway may each be approximated by a first and second vector, respectively. The angle between the first determined surgical pathway and the second determined surgical pathway may be calculated using the following relationship:

$$\cos(\theta)=A\cdot B/\|A\|\|B\|$$

where A denotes the first vector, B denotes the second vector, A·B is the scalar product of vectors A and B, and ∥A∥ denotes the magnitude of vector A.

To approximate the surgical pathway as a vector, the surgical portal may be approximated as a point in the model. For example, the surgical portal may be approximated as a point with (x,y,z) coordinates. To approximate the surgical portal, the center of the volume defined by the surgical portal may be determined. Similarly, the surgical target region may be approximated as a single point in the model. For example, the surgical target region may be approximated as a point with (x,y,z) coordinates. To approximate the surgical target region, the center of the volume defined by the surgical target region may be determined. When both the surgical portal and the surgical target region are approximated as points in the model, the surgical pathway involving the surgical portal and the surgical target region may be approximated as a vector extending from the point approximating the surgical portal to the point approximating the surgical target region.

In other embodiments, the approach characteristic may be a qualitative quality that may cause a particular surgical approach to be more or less appropriate for the particular surgery. In some embodiments, a surgical approach that results in inappropriate displacement of or collateral damage to neighboring anatomical structures may be assigned an approach characteristic indicating that qualitative quality. For example, a surgical approach may include a first determined surgical pathway and a second determined surgical pathway where both the surgical pathways include surgical portals involving the same orbit, such as the left superior lid crease and the left precaruncular. Such a surgical approach may involve inappropriate displacement of or damage to the eye or orbit, among other possibilities.

Figure 7:
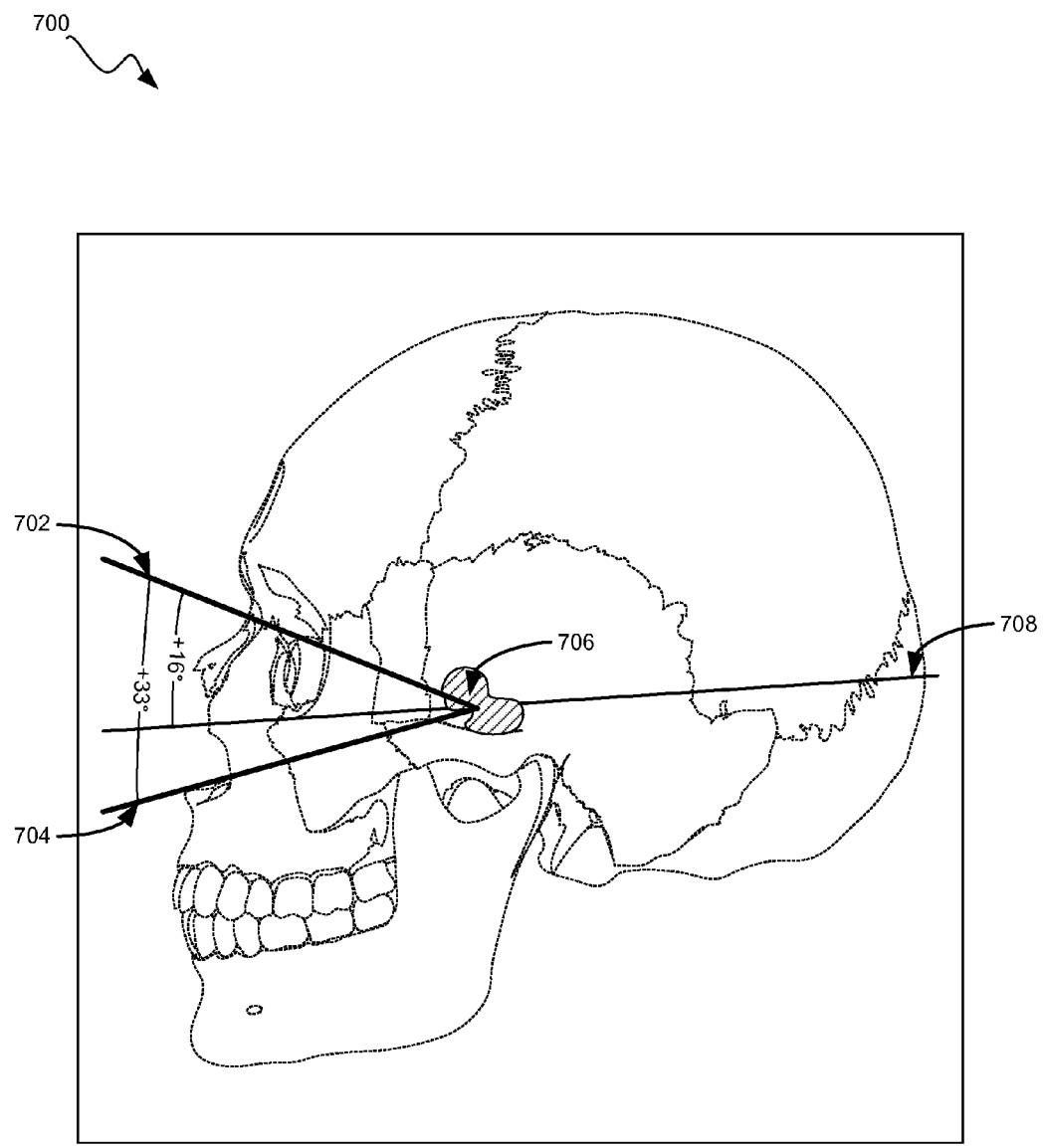
FIG. 7 shows illustrative surgical pathways and an illustrative anatomical plane within an illustrative three-dimensional model of a human skull.

FIG. 7 depicts an illustration of a model of a skull 700, as shown in a side-view. FIG. 7 further depicts surgical pathways 702 and 704 extending from a surgical portal to a surgical target region 706. For the purposes of explanation, surgical pathways 702 and 704 are approximated as vectors in FIG. 7. Surgical pathway 702 involves the left superior lid crease portal. Surgical pathway 704 involves the left transnasal portal. The calculated angle between surgical pathway 702 and surgical pathway 704 is 33°, as shown. Surgical pathways 702 and 704 are provided by way of example only, and should not be taken as limiting. Many other examples of surgical pathways are possible.

i. Determining Approach Characteristics in the Study of Fourteen Subjects.

Figure 8:
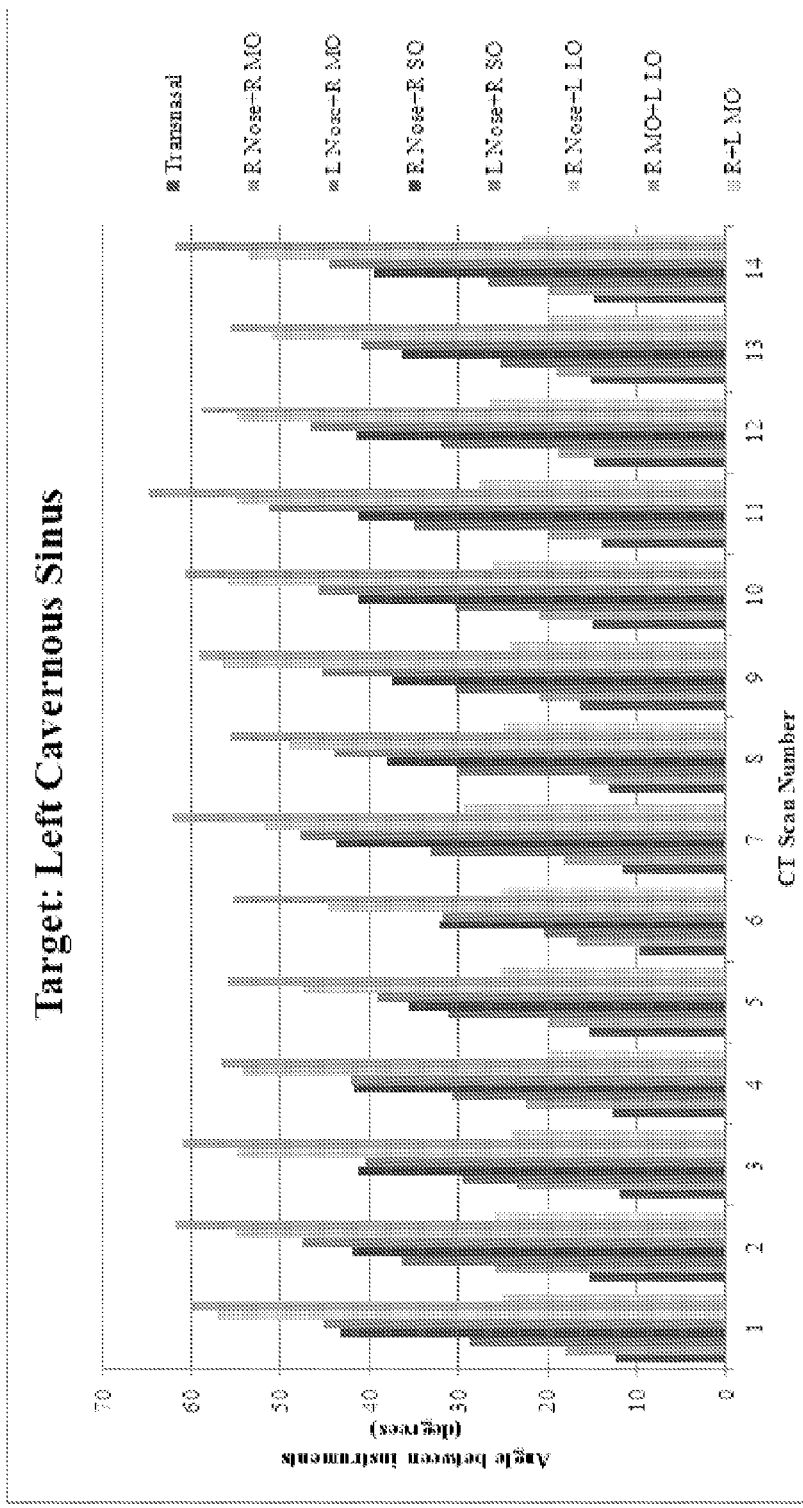
FIG. 8 shows a chart that provides angles between instruments in a study of fourteen subjects.

In the study of fourteen subjects, angulations between two surgical pathways in the eight determined surgical approaches were calculated for each of the fourteen subjects. The results are shown in FIG. 8. The possible angles between instruments ranged from 13.9° in the case of two transnasal portals, to 58.7° when a combination of medial and lateral orbit portals was involved. In FIG. 8, transnasal refers to the left and right transnasal. R to right, L to left, nose to transnasal. MO to medial orbit, and LO to lateral orbit.

e. Determine at Least One Pathway Characteristic

At block 310, for each surgical approach in the plurality of surgical approaches, and for each determined surgical pathway in the respective surgical approach, the computing system determines at least one pathway characteristic. In some embodiments, for each determined surgical pathway, the at least one determined pathway characteristic includes at least one of: (a) a pathway length; (b) an angulation between the determined surgical pathway and an anatomical plane: (c) a volume of the determined surgical pathway; (d) an intersected anatomical structure; or (e) a distance that an anatomical structure is displaced to provide the surgical pathway. In various embodiments, the pathway characteristic may include at least one of, all of, or any combination of (a)-(e). In some embodiments, the pathway characteristic may be a quality that may cause a particular surgical pathway to be more or less appropriate for the particular surgery.

In some embodiments, the at least one pathway characteristic may include an angulation (or angle) between the determined surgical pathway and an anatomical plane. In some circumstances, the angle between the particular surgical pathway and a particular anatomical plane may cause that particular surgical pathway to be more or less appropriate for the particular surgery.

The anatomical plane may include any anatomical plane that may be defined in the model. For example, the anatomical plane may include a midsagittal plane or a skull base plane. In some embodiments, the anatomical plane may be defined by choosing two sets of data points in the 3-d model and then extending a plane between the two sets of data points. For example, where the model defines a skull, the midsaggital plane and the skull base may be defined by choosing data points at the crista galli and the posterior internal occipital protuberance, and between the posterior clinoid processes and the tuberculum sellae, respectively. Though anatomical planes relating to the skull have been provided as examples, anatomical planes related to other portions of the body may be defined as well.

Returning to FIG. 7, FIG. 7 further depicts anatomical plane 708. Anatomical plane involves the skull base plane. The calculated angle between anatomical plane 708 and surgical pathway 702 is 16°, as shown. Anatomical plane 708 and surgical pathway 702 are provided by way of example only, and should not be taken as limiting. Many other examples of surgical pathways and anatomical planes are possible.

In some embodiments, the pathway characteristic may include a pathway length. For each determined surgical pathway in the respective surgical approach, the pathway length may be the distance from the surgical portal to the surgical target region. As noted above, in some embodiments, the surgical pathway may be approximated as a vector. In such embodiments, the pathway length may be the magnitude of the vector. In other embodiments, the length of the pathway may be calculated based on the distance between the point in the surgical portal and the point in the surgical target region that are furthest from one another, among other possible techniques.

In some circumstances, a shorter pathway length may cause a particular surgical pathway to be more appropriate because a shorter pathway length may cause less pathway trauma. Similarly, a longer pathway length may cause a particular surgical pathway to be less appropriate because a shorter pathway length may cause more pathway trauma.

In other embodiments, the pathway characteristic may include a volume of the determined surgical pathway. As noted above, in some embodiments, the determined surgical pathway defines a volume in the model. The volume of the surgical pathway may be determined by determining the number of voxels in that define the volume and then multiplying by the physical size that each voxel represents. For example, a voxel may represent a space 1 millimeter (mm)×1 mm×1 mm. Therefore, a surgical pathway defining a volume including, for example, 10,000 voxels, may have a volume of 10,000 cubic millimeters (10 cubic centimeters). Other techniques for determining the volume of the determined surgical pathway are possible as well.

In some embodiments, a larger volume may indicate that a particular surgical pathway is more appropriate. For example, the larger volume may better accommodate surgical instruments. However, in other circumstances, a particular surgical instrument may not require a larger volume. In other circumstances, a smaller volume may indicate that a particular surgical pathway is less appropriate.

In further embodiments, the volume of the determined surgical pathway may indicate the area of a cross-section. The area of a cross-section of a particular surgical pathway may be determined by calculating the number of voxels that are included in a cross-section of the defined volume of a particular surgical pathway. A larger cross-section may indicate that a particular surgical pathway is more appropriate. For example, the larger cross-section may better accommodate surgical instruments. In other circumstances, a smaller cross-section may indicate that a particular surgical pathway is less appropriate.

In some embodiments, the pathway characteristic may include an intersected anatomical structure. In some circumstances, intersection of a particular anatomical structure may be inappropriate. For example, a particular surgical pathway that intersects a particular anatomical structure may cause unacceptable damage to that intersected anatomical structure. In such an example, the pathway characteristic that includes an intersected anatomical structure may indicate that the particular surgical pathway is less appropriate.

In some embodiments, the pathway characteristic may include a distance that an anatomical structure is displaced to provide the surgical pathway. For example, where the model provides a representation of a skull, a surgical pathway may require displacement of the eye to form the surgical pathway involving a transorbital portal. The distance of displacement of the anatomical feature may indicate that a particular surgical approach is more or less appropriate. For example, where the eye is displaced to form the surgical pathway involving the transorbital portal, some extent of displacement of the eye may be appropriate; however, a greater extent of displacement may be inappropriate.

i. Determining Pathway Characteristics in the Study of Fourteen Subjects.

Figure 9:
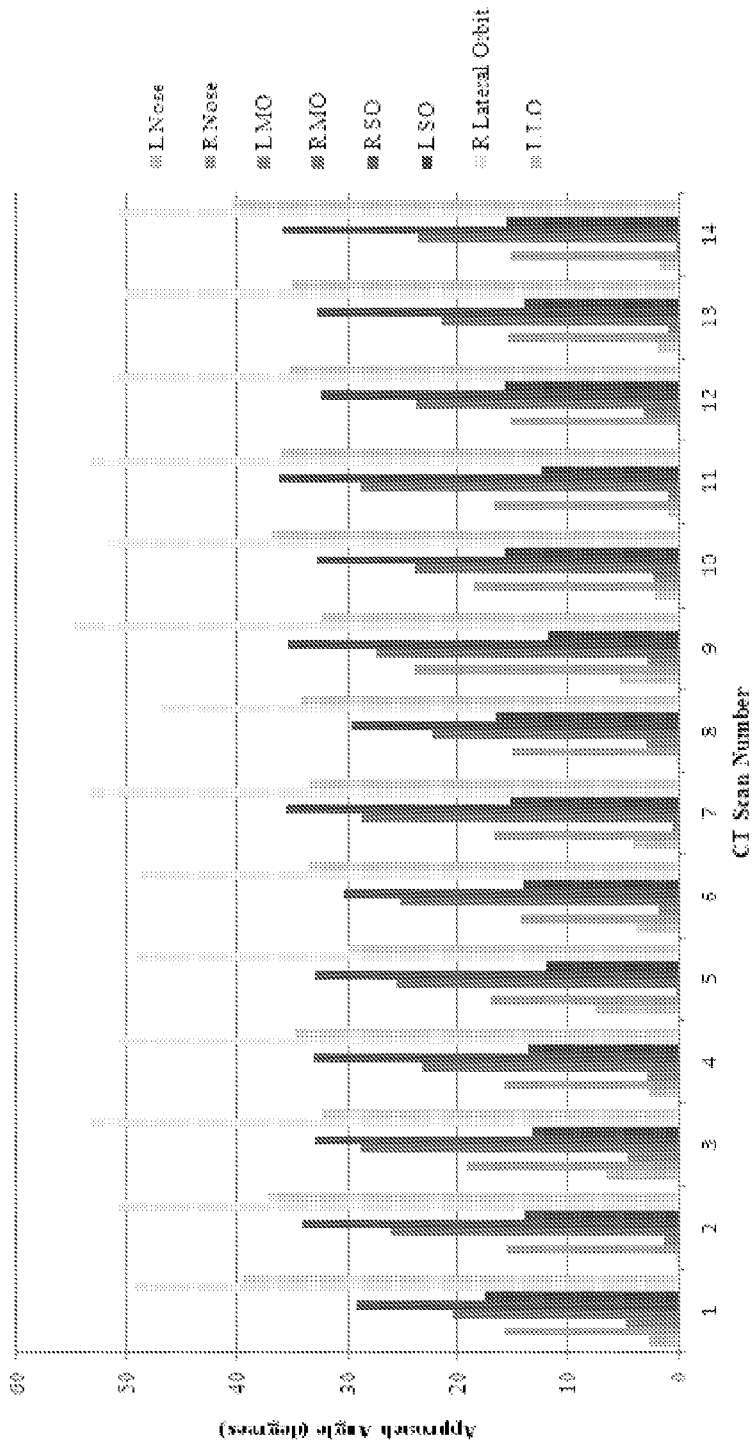
FIG. 9 shows a chart that provides angles between instruments and an anatomical plane in the study of fourteen subjects.

In the study of fourteen subjects, for each of eight determined surgical pathways, an angulation between the respective surgical pathway to the left cavernous sinus with respect to the midsagittal plane was calculated for each of the fourteen subjects. The results are shown in FIG. 9. The range of possible angles between the pathway and the plane was approximately 60°. In FIG. 9, R refers to right, L to left, nose to transnasal, MO to medial orbit, SO to superior orbit, and LO to lateral orbit.

ii. Determining Additional Approach and Pathway Characteristics in the Study of Fourteen Subjects.

In the study of fourteen subjects, approach and pathway characteristics for additional surgical target regions located within the skull were determined. FIG. 11 presents approach and pathway characteristics for non-midline surgical targets regions including the cavernous sinus, Meckel's cave, and the superior optic fissure. The symmetric surgical approach combinations for each surgical target region were averaged. For example, the approach and pathway characteristics from the left transnasal and right medial orbit surgical approach to reach a left side surgical target region were averaged with the right transnasal and left medial orbit surgical approach to reach a right side surgical target region.

FIG. 12 presents approach and pathway characteristics for midline surgical targets regions including the prechiasmatic, postchiasmatic, third ventricle, basal cistern, and clivus. Like the non-midline surgical target regions, the symmetric surgical approach combinations for each surgical target region were averaged.

f. Determine a Surgical Approach Ranking

Turning to FIG. 3B, method 300 continues with block 312, where, for each surgical approach in the plurality of surgical approaches, the computing system determines a surgical-approach ranking based on the determined at least one approach characteristic and the determined at least one pathway characteristic. As noted above, the approach characteristics and pathway characteristics may cause particular surgical approaches and surgical pathways of the particular surgical approaches to be more or less appropriate. These approach characteristics and pathway characteristics may be used to determine a surgical approach ranking for each determined surgical approach.

In some embodiments, the determined surgical approaches in the plurality of surgical approaches may be numerically ranked. For example, if there are 100 determined surgical approaches in the plurality of surgical approaches, each determined surgical approaches in the plurality of surgical approaches may be assigned a rank from 1-100.

In some embodiments, the at least one approach characteristic of each respective surgical approach in the plurality of surgical approaches may be assigned a numerical value to assist in determining the surgical ranking of each surgical approach. For example, a particular approach characteristic including an angulation between surgical instruments of more than 15 degrees may be assigned a numerical value that indicates a relatively more appropriate surgical approach than another approach characteristic including an angulation between surgical instruments of less than 15 degrees. Similarly, the at least one pathway characteristic of each respective surgical pathway in each respective particular surgical approach in the plurality of surgical approaches may be assigned a numerical value to assist in determining the surgical ranking of each surgical approach. For example, a particular pathway characteristic having a pathway length of 50 mm may be assigned a numerical value that indicates a relatively more appropriate surgical approach than another pathway characteristic including having a pathway length of 100 mm.

The at least one approach characteristic and the at least one pathway characteristic may be weighted. For example, an approach characteristic including an angulation between surgical instruments of more than 15 degrees may cause a particular surgical approach to have a relatively higher ranking than another approach or pathway characteristic, such as a relatively short pathway length.

The above techniques for determining a surgical approach ranking are provided for example and explanation only and should not be taken as limiting. One having skill in the art will appreciate that there may be many techniques for ranking surgical approaches each having characteristics that may be used for comparison among surgical approaches.

g. Select a Subset of Plurality of Surgical Approaches

At block 314, the computing system selects a subset of the plurality of surgical approaches based on the determined surgical approach rankings. In some embodiments, the subset may be the group of surgical approaches used in practice, such as during surgery or in preparing for surgery. In other embodiments, the subset may be a group from which a user, such as a surgeon, chooses which surgical approaches to use in practice, such as during surgery.

In some embodiments, the subset of the plurality of surgical approaches may include one surgical approach. For example, the surgical approach in the plurality of surgical approaches with the highest ranking may be selected to be the subset of the plurality of surgical approaches. In some embodiments, the one surgical approach in the subset the plurality of surgical approaches may be used during surgery. The surgery may be virtual or physical.

In other embodiments, the subset of the plurality of surgical approaches may include more than one surgical approach. For example, the surgical approaches in the plurality of surgical approaches with the five highest rankings may be selected to be the subset of the plurality of surgical approaches. Or, the surgical approaches in the plurality of surgical approaches with the ten highest rankings may be selected to be the subset of the plurality of surgical approaches. The number of surgical approaches in the subset of the plurality of surgical approaches may vary. In some embodiments, that computing system may be configured to include a particular number of surgical approaches in the subset of the plurality of surgical approaches.

i. Selecting a Subset of the Plurality of Surgical Approaches in the Study of Fourteen Subjects.

Figure 13:
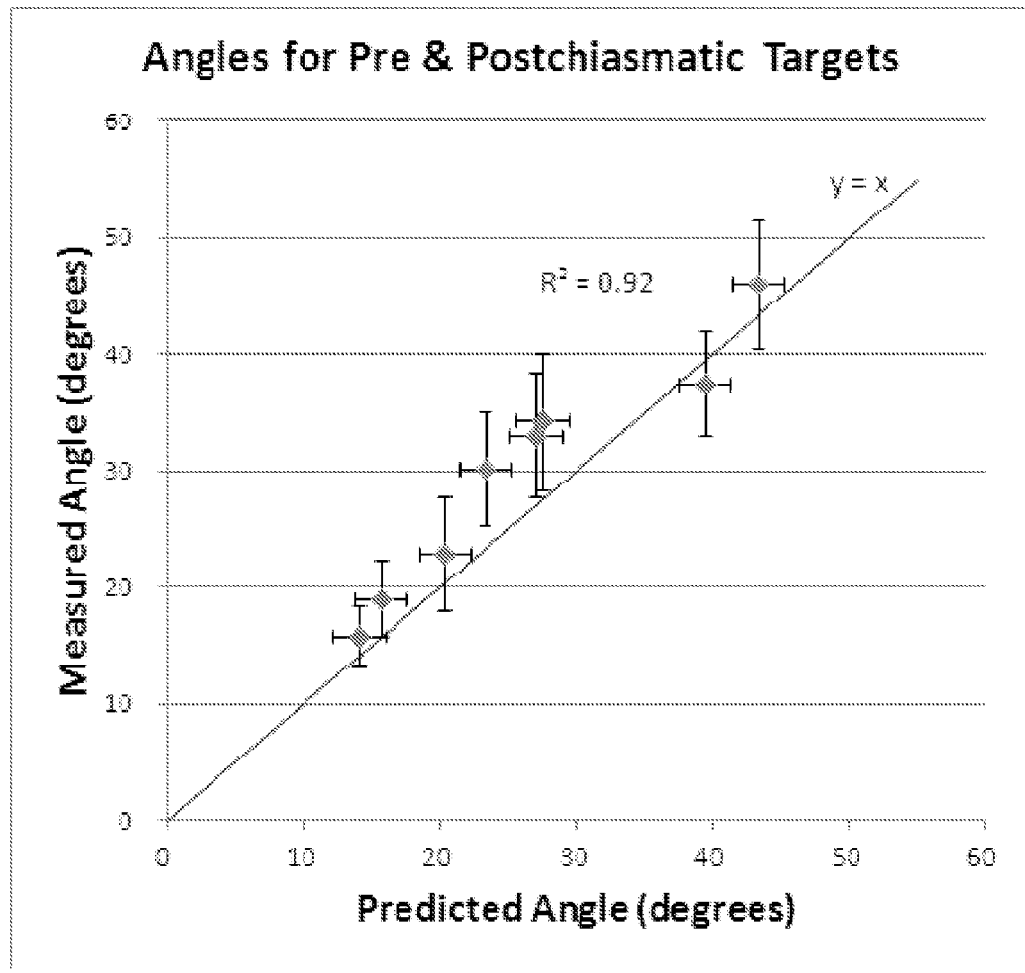
FIG. 13 shows a plot comparing determined approach characteristics to measured approach characteristics.
Figure 14:
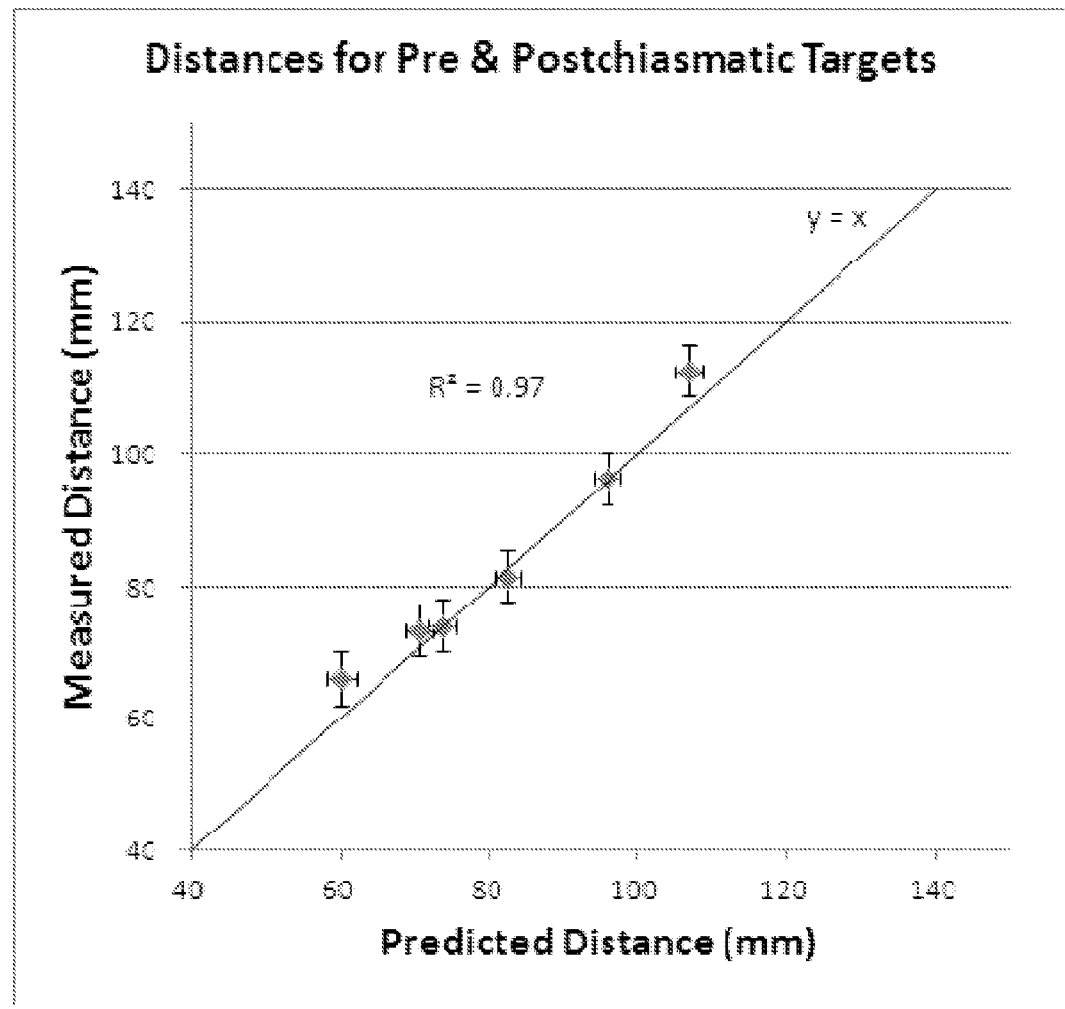
FIG. 14 shows a plot comparing determined pathway characteristics to measured approach characteristics.
Figure 15:
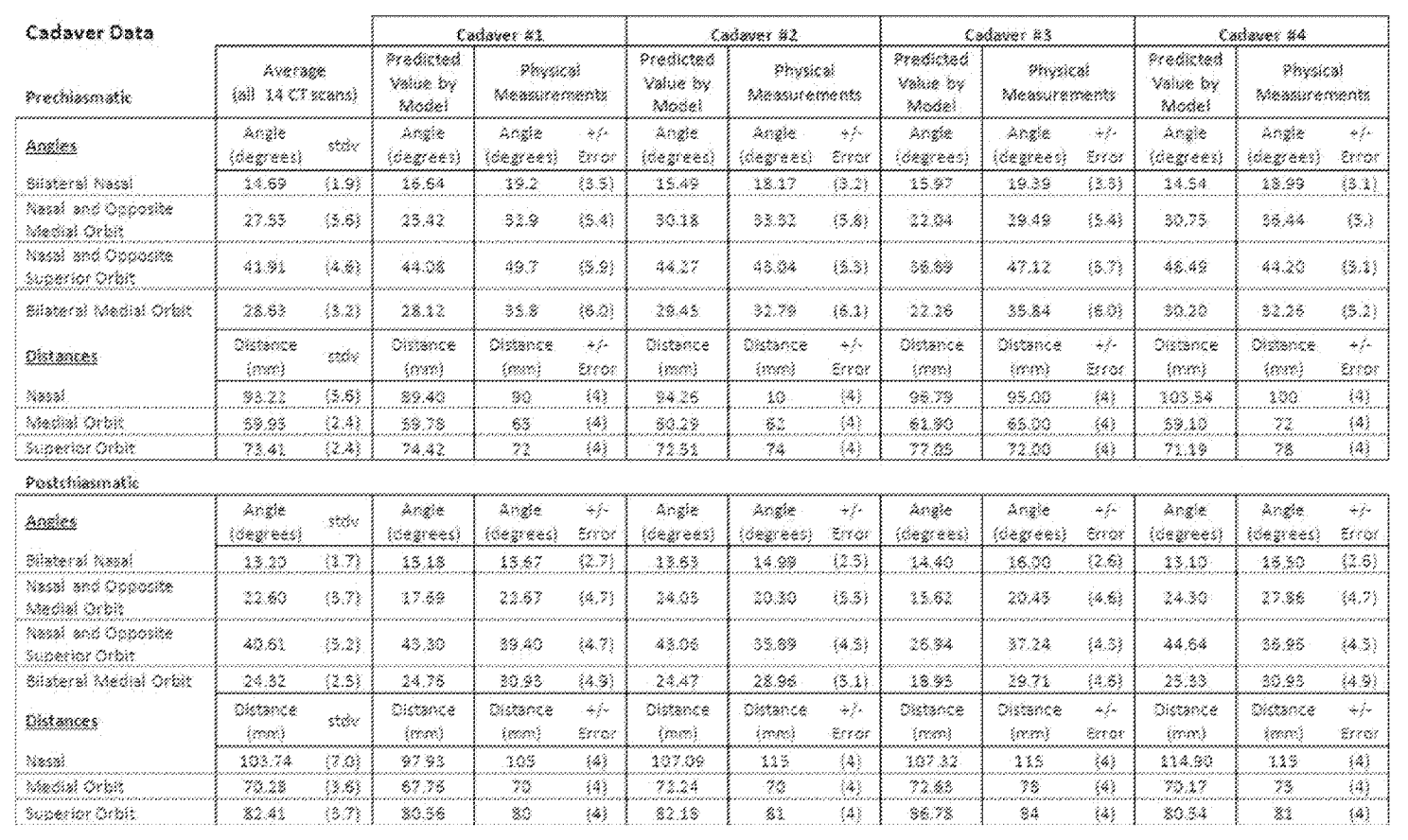

In the study of fourteen subjects, a subset of surgical approaches was selected, and the selected surgical approaches for each surgical target region were performed on four cadavers. Physical approach and pathway characteristics for each respective surgical approach were measured. The results are presented in FIG. 15. Comparisons of the determined approach characteristics versus the physical measurements are shown in FIGS. 13 and 14. FIG. 13 presents the determined angulation (angles) between determined surgical pathways in each surgical approach versus the measured angles in a scatterplot showing standard deviation and measurement error. Similarly, FIG. 14 presents the determined pathway length (distance) for each surgical pathway in each surgical approach versus the measured lengths in a scatterplot showing standard deviation and measurement error. Both FIG. 13 and FIG. 14 show that the determined values were highly correlated to the actual values. Specifically, the determined angulation (angles) between determined surgical pathways in each surgical approach versus the measured angles had an $R^2$ value of 0.91, and the determined pathway length (distance) for each surgical pathway in each surgical approach versus the measured lengths had an $R^2$ value of 0.97.

g. Cause Output Device to Provide a Representation of Selected Subset

At block 316, the computing system causes an output device to provide a representation of the selected subset of the plurality of surgical approaches. For example, computing system 100 may cause output device 120 to provide a representation of the selected subset of the plurality of surgical approaches.

In some embodiments, the output device includes a graphical display. In such embodiments, causing the graphical display to provide the representation may involve causing the graphical display to provide a three-dimensional graphical representation of the determined representation. This arrangement may display the three-dimensional graphical representation to the surgeon during the performance or planning of the surgery.

In other embodiments, the output device includes an additive manufacturing machine. In such embodiments, causing the additive manufacturing machine to make the representation may involve causing the additive manufacturing machine to provide a physical representation of the determined representation.

In some embodiments, the representation provided by the output device may be modular, such that the representation may include components that may be combined to form the physical representation. In some embodiments, the representation may be disassembled into components. The modular representation may be a physical representation or a graphical representation, among other possibilities.

In some embodiments, the components may include physical representations of anatomical features. As noted above, the model may be provided by normalizing data from multiple medical images of different patients to form the representative model. Similarly, anatomical features represented within the model may be provided by normalizing data from multiple medical images of different patients. Such anatomical features may be re-used from patient to patient.

FIG. 10 depicts a representation 1000 of a model of a human skull. Representation 1000 is modular such that the model includes components that may be combined to form the representation. Representation 1000 may be a physical representation or a graphical representation, among other possibilities.

In some embodiments, the computing system determines a surgical plan based on the selected subset of surgical approaches. The surgical plan may be a particular surgical approach used during the surgery. As noted above, the surgery may be surgery on a patient or virtual surgery on a simulated patient. In some embodiments, the computing system may include the highest ranked surgical approach in the subset of surgical approaches in the surgical plan. In other embodiments, the computing system may receive data indicating the appropriate surgical approach to include in the surgical plan. In some embodiments, the data indicating the appropriate surgical approach may be sent from an input device, such as a touchscreen or a mouse and keyboard.

In some embodiments, the computing system causes a surgical instrument to move based on the selected subset of surgical approaches. For example, the computing system may cause a computer-assisted surgical instrument to move based on the selected subset of surgical approaches. Or, the computing system may cause a robotic surgical instrument to move based on the selected subset of surgical approaches. Such instruments may be configured to act in relation to the surgical target region.

In some embodiments, the surgical instrument may be coupled to a surgical navigation system. In such embodiments, causing the surgical instrument to move based on the selected subset may involve sending data representing the selected subset of surgical approaches to one or more surgical navigation systems. In some embodiments, the surgical navigation system may be configured to move the surgical instrument based on the data representing the selected subset of surgical approaches. In other embodiments, the surgical navigation system may be configured to prevent movement of surgical instruments based on the data representing the selected subset of surgical approaches. The computing system may also send data representing elements, such as the one or more anatomical structures, in the model to the one or more surgical navigations system.

In some embodiments, the computing system may cause the representation of the selected set of the plurality of surgical approaches to be displayed on a display of a surgical navigation system. The surgical navigation system may be coupled to an endoscope that provides an image stream. The representation of the selected set of the plurality of surgical approaches may be overlaid (i.e. superimposed) on the image stream. This arrangement may allow the relative position of the endoscope to be compared to the selected set of the plurality of surgical approaches.

In some embodiments, the surgical instrument may be a virtual instrument. In such embodiments, the surgical instrument may be represented in the model. The surgical instrument may move within the 3-d coordinate system defined by the model. For example, the surgical instrument may move within the volume defined by the surgical pathway. In some embodiments, the surgical instrument is configured for one or more functions. For example, a drill may be configured to bore holes. A virtual surgical instrument that is configured for one or more functions may be functional within the model. Such an arrangement may simulate surgery or a component thereof.

In some embodiments, the surgical instrument may be an endoscope. The endoscope may be a physical endoscope or a virtual endoscope. In some embodiments, causing a surgical instrument to move based on the selected subset of surgical approaches may involve causing the endoscope to move based on the selected subset of surgical approaches. When the surgical instrument is a virtual endoscope, causing a surgical instrument to move based on the selected subset of surgical approaches may be referred to as virtual endoscopy. In further embodiments, the output device may be a graphical display, as noted above. The graphical display may provide a representation of the model from the point of view of the endoscope to simulate endoscopy. In some embodiments, the representation may change as the endoscope is moved. For example, the representation may reflect the point of view of the endoscope as the endoscope is moved down a determined surgical pathway.

In some embodiments, the selected subset of surgical approaches may indicate physical coordinates. The surgical instrument may move according to the physical coordinates. The surgical instrument may move in relation to the determined surgical approach. For example, the surgical instrument may move along the surgical pathway to act in relation to the surgical target region.

In some embodiments, causing a surgical instrument to move based on the selected subset of surgical approaches involves sending data indicating surgical approach coordinates to a surgical instrument. For example, computing system 100 in FIG. 1 may send the data indicating the selected subset of surgical approaches over system bus, network, or other connection mechanism 112. In such embodiments, the data indicating surgical approach coordinates may be arranged to cause a surgical instrument to move based on the selected subset of surgical approaches. Other examples are possible as well.

In some embodiments, the computing system causes the output device to provide a pathway protection element based on a determined surgical pathway of the one or more surgical approaches in the selected subset of the plurality of surgical approaches, where the pathway protection element is configured for insertion in the determined surgical pathway. Such an arrangement may reduce the risk of pathway trauma during surgery, in some circumstances. The pathway protection element may be physical, virtual, or graphical, among other possibilities.

In some embodiments, the pathway protection element may include data indicating one or more lock-ins and/or lock-outs. Lock-outs may indicate regions of the model into which a surgical instrument may be prevented from moving. Lock-ins may indicate regions of the model that a surgical instrument may be prevented from moving out of. For example, a particular surgical pathway may be identified as a lock-in and a particular surgical instrument may be prevented from moving out of that surgical pathway. In some embodiments, anatomical structures in the model may be identified as lock-outs.

In embodiments when the computing system causes a surgical instrument to move based on the selected subset of surgical approaches, the lock-ins and/or lock-outs may prevent the surgical instrument from moving out of or into particular regions, such as particular anatomical structures. In other embodiments, a warning may be provided when a surgical instrument approaches the boundary of a lock-in or lock-out. In an embodiment, the surgical margin may be a lock-in. For example, a particular surgical instrument used to excise a particular target pathology may be prevented from moving outside of the tumor margin. This arrangement may guide movement of a surgical instrument. For example, to excise a tumor, the surgeon may move a surgical instrument along borders of the lock-in region. The surgeon's movements may be guided (or limited) by the extent of the lock-in region. This arrangement may reduce the risk of damage to tissues surrounding the target pathology, among other potential benefits.

In some embodiments, the computing system may receive data representing a performed surgery. The data representing the performed surgery may include data indicating movement of one or more surgical instruments used during the surgery. In some embodiments, the data may also include the position, acceleration, and velocity of surgical instruments used during the surgery.

In some embodiments, the computing system may determine one or more surgical performance parameters based on the data indicating the performed surgery. The surgical performance parameters may include, for example, time duration of the surgery, a number of surgical instruments used during the surgery, a number of surgical pathway violations, and a number of warnings provided during the surgery. The data indicating the performed surgery and/or the surgical performance parameters may be stored by the computing system, a remote server, or by another type of storage device. In some embodiments, the surgical performance parameters from a particular surgery may be used to evaluate the surgery. In further embodiments, surgical performance parameters determined from data received from different performed surgeries may be used to track the surgical performance parameters over time, such as to track the progress of a particular surgeon. In some embodiments, the performed surgery may be assigned a score based on the determined one or more surgical performance parameters.

In some embodiments, the output device may provide a representation of an implant based on the model. For example, the model may indicate an anatomical structure for which an implant may be appropriate, such as a fractured bone or an anatomical defect. The representations may be physical or graphical. The provided representation of an implant may be used during the surgery to repair the damaged anatomical structure. For example, a provided physical representation, such as an orbital floor fracture repair implant, may be used at the time of surgery.

3. CONCLUSION

While various aspects and embodiments have been disclosed herein, other aspects and embodiments will be apparent to those skilled in the art. For example, with respect to the flow charts depicted in the figures and discussed herein, functions described as blocks may be executed out of order from that shown or discussed, including substantially concurrent or in reverse order, depending on the functionality involved. Further, more or fewer blocks and/or functions may be used and/or flow charts may be combined with one another, in part or in whole.

The various aspects and embodiments disclosed herein are for purposes of illustration and are not intended to be limiting, with the true scope and spirit being indicated by the following claims. Other embodiments can be utilized, and other changes can be made, without departing from the spirit or scope of the subject matter presented herein.

We claim:

1. A computer-implemented method comprising:
receiving data indicating (a) one or more surgical target regions and (b) one or more surgical portals using a computing system;
determining a plurality of surgical pathways using the computing system, wherein each surgical pathway in the plurality of surgical pathways comprises (a) a respective surgical target region of the one or more surgical target regions and (b) a respective surgical portal of the one or more surgical portals;
determining a plurality of surgical approaches using the computing system, wherein each surgical approach in the plurality of surgical approaches comprises at least a first determined surgical pathway;
for each surgical approach in the plurality of surgical approaches:
  determining at least one approach characteristic using the computing system,
  for each determined surgical pathway in the respective surgical approach, determining at least one pathway characteristic using the computing system, and
  determining a surgical-approach ranking based on the determined at least one approach characteristic and the determined at least one pathway characteristic using the computing system;
wherein one or more surgical approaches in the plurality of surgical approaches further comprise a second determined surgical pathway, and wherein the at least one determined approach characteristic comprises an angulation between the first determined surgical pathway and the second determined surgical pathway;
selecting a subset of the plurality of surgical approaches based on the determined surgical approach rankings using the computing system;

causing an output device of the computing system to provide a representation of the selected subset of the plurality of surgical approaches;
causing the output device to provide at least a graphical pathway protection element based on a determined surgical pathway of one or more surgical approaches in the selected subset of the plurality of surgical approaches, wherein the pathway protection element is related to insertion of a surgical instrument in the determined surgical pathway, wherein the pathway protection element indicates one or more lock-outs indicating one or more regions where the surgical instrument is prevented from moving into and/or one or more lock-ins indicating one or more regions where the surgical instrument is prevented from moving from; and
providing one or more warnings using the computing system, the one or more warnings provided when the surgical instrument approaches a boundary of at least one of the one or more lock-outs and/or the one or more lock-ins.

2. The method of claim 1, wherein the output device comprises a graphical display, and wherein causing the graphical display to provide the representation comprises causing the graphical display to provide a three-dimensional graphical representation of the determined representation.

3. The method of claim 1, wherein the output device comprises an additive manufacturing machine; and wherein causing the additive manufacturing machine to make the representation comprises causing the additive manufacturing machine to provide a physical representation of the determined representation.

4. The method of claim 1, further comprising:
receiving, at the computing device, data including one or more surgical performance parameters regarding a performed surgery; and
generating a score for the performed surgery using the computing device, the score based on the one or more surgical performance parameters.

5. The method of claim 1, wherein, for each determined surgical pathway, the at least one determined pathway characteristic comprises at least one of: (a) a pathway length; (b) an angulation between the determined surgical pathway and an anatomical plane; (c) a volume of the determined surgical pathway; (d) an intersected anatomical structure; or (e) a distance that an anatomical structure is displaced to provide the surgical pathway.

6. The method of claim 1, further comprising:
causing a surgical instrument to move based on the selected subset of surgical approaches.

7. A computing system comprising:
an output device;
a physical computer readable medium; and
program instructions stored on the physical computer readable medium and executable by at least one processor to:
  receive data indicating (a) one or more surgical target regions and (b) one or more surgical portals;
  determine a plurality of surgical pathways, wherein each surgical pathway in the plurality of surgical pathways comprises (a) a respective surgical target region of the one or more surgical target regions and (b) a respective surgical portal of the one or more surgical portals;

determine a plurality of surgical approaches, wherein each surgical approach in the plurality of surgical approaches comprises at least a first determined surgical pathway;

for each surgical approach in the plurality of surgical approaches,
  determine at least one approach characteristic,
  for each determined surgical pathway in the respective surgical approach, determine at least one pathway characteristic, and
  determine a surgical-approach ranking based on the determined at least one approach characteristic and the determined at least one pathway characteristic;

wherein one or more surgical approaches in the plurality of surgical approaches further comprise a second determined surgical pathway, and wherein the at least one determined approach characteristic comprises an angulation between the first determined surgical pathway and the second determined surgical pathway;

select a subset of the plurality of surgical approaches based on the determined surgical approach rankings;

cause the output device to provide a representation of the selected subset of the plurality of surgical approaches;

cause the output device to provide at least a graphical pathway protection element based on a determined surgical pathway of one or more surgical approaches in the selected subset of the plurality of surgical approaches, wherein the pathway protection element is related to insertion of a surgical instrument in the determined surgical pathway, wherein the pathway protection element indicates one or more lock-outs indicating one or more regions where the surgical instrument is prevented from moving into and/or one or more lock-ins indicating one or more regions where the surgical instrument is prevented from moving from; and provide one or more warnings when the surgical instrument approaches a boundary of at least one of the one or more lock-outs and/or the one or more lock-ins.

8. The computing system of claim 7, wherein the output device comprises a graphical display, and wherein causing the graphical display to provide the representation comprises causing the graphical display to provide a three-dimensional graphical representation of the determined representation.

9. The computing system of claim 7, wherein the output device comprises an additive manufacturing machine; and wherein causing the additive manufacturing machine to make the representation comprises causing the additive manufacturing machine to provide a physical representation of the determined representation.

10. The computing system of claim 7, wherein the program instructions are further executable by at least one processor to:
  receive data including one or more surgical performance parameters regarding a performed surgery; and
  generate a score for the performed surgery, the score based on the one or more surgical performance parameters.

11. The computing system of claim 7, wherein, for each determined surgical pathway, the at least one determined pathway characteristic comprises at least one of: (a) a pathway length; (b) an angulation between the determined surgical pathway and an anatomical plane; (c) a volume of the determined surgical pathway; (d) an intersected anatomical structure; or (e) a distance that an anatomical structure is displaced to provide the surgical pathway.

12. The computing system of claim 7, wherein the program instructions are further executable by at least one processor to:
  cause a surgical instrument to move based on the selected subset of surgical approaches.

13. A physical computer readable medium having stored therein instructions executable by a computing system to cause the computing system to perform functions comprising:
  receiving data indicating (a) one or more surgical target regions and (b) one or more surgical portals;
  determining a plurality of surgical pathways, wherein each surgical pathway in the plurality of surgical pathways comprises (a) a respective surgical target region of the one or more surgical target regions and (b) a respective surgical portal of the one or more surgical portals;
  determining a plurality of surgical approaches, wherein each surgical approach in the plurality of surgical approaches comprises at least a first determined surgical pathway;
  for each surgical approach in the plurality of surgical approaches,
    determining at least one approach characteristic,
    for each determined surgical pathway in the respective surgical approach, determining at least one pathway characteristic, and
    determining a surgical-approach ranking based on the determined at least one approach characteristic and the determined at least one pathway characteristic;
  wherein one or more surgical approaches in the plurality of surgical approaches further comprise a second determined surgical pathway, and wherein the at least one determined approach characteristic comprises an angulation between the first determined surgical pathway and the second determined surgical pathway;
  selecting a subset of the plurality of surgical approaches based on the determined surgical approach rankings;
  causing an output device to provide a representation of the selected subset of the plurality of surgical approaches;
  causing the output device to provide at least a graphical pathway protection element based on a determined surgical pathway of one or more surgical approaches in the selected subset of the plurality of surgical approaches, wherein the pathway protection element is related to insertion of a surgical instrument in the determined surgical pathway, wherein the pathway protection element indicates one or more lock-outs indicating one or more regions where the surgical instrument is prevented from moving into and/or one or more lock-ins indicating one or more regions where the surgical instrument is prevented from moving from; and
  providing one or more warnings when the surgical instrument approaches a boundary of at least one of the one or more lock-outs and/or the one or more lock-ins.

14. The physical computer readable medium of claim 13, wherein the output device comprises a graphical display, and wherein causing the graphical display to provide the representation comprises causing the graphical display to provide a three-dimensional graphical representation of the determined representation.

15. The physical computer readable medium of claim 13, wherein the output device comprises an additive manufacturing machine; and wherein causing the additive manufacturing machine to make the representation comprises causing the additive manufacturing machine to provide a physical representation of the determined representation.

16. The physical computer readable medium of claim 13, wherein the functions further comprise:
- receive data including one or more surgical performance parameters regarding a performed surgery; and
- generate a score for the performed surgery, the score based on the one or more surgical performance parameters.

17. The physical computer readable medium of claim 13, wherein, for each determined surgical pathway, the at least one determined pathway characteristic comprises at least one of: (a) a pathway length; (b) an angulation between the determined surgical pathway and an anatomical plane; (c) a volume of the determined surgical pathway; (d) an intersected anatomical structure; or (e) a distance that an anatomical structure is displaced to provide the surgical pathway.

18. The physical computer readable medium of claim 13, wherein the functions further comprise:
- causing a surgical instrument to move based on the selected subset of surgical approaches.

* * * * *